(12) United States Patent
Kolkhof et al.

(10) Patent No.: US 11,331,308 B2
(45) Date of Patent: May 17, 2022

(54) COMBINATION CONTAINING SGC ACTIVATORS AND MINERALOCORTICOID RECEPTOR ANTAGONISTS

(71) Applicant: BAYER PHARMA AKTIENGESELLSCHAFT, Berlin (DE)

(72) Inventors: Peter Kolkhof, Wuppertal (DE); Peter Sandner, Wuppertal (DE)

(73) Assignee: BAYER PHARMA AKTIENGESELLSCHAFT, Berlin (DE)

(*) Notice: Subject to any disclaimer, the term of this patent is extended or adjusted under 35 U.S.C. 154(b) by 0 days.

(21) Appl. No.: 16/337,020

(22) PCT Filed: Oct. 5, 2017

(86) PCT No.: PCT/EP2017/075356
§ 371 (c)(1),
(2) Date: Mar. 27, 2019

(87) PCT Pub. No.: WO2018/069148
PCT Pub. Date: Apr. 19, 2018

(65) Prior Publication Data
US 2019/0224176 A1 Jul. 25, 2019

(30) Foreign Application Priority Data
Oct. 11, 2016 (EP) .................................... 16193367

(51) Int. Cl.
| | | |
|---|---|---|
| *C07D 471/04* | (2006.01) | |
| *A61K 31/4375* | (2006.01) | |
| *A61K 45/06* | (2006.01) | |
| *A61K 31/167* | (2006.01) | |
| *A61K 31/4365* | (2006.01) | |
| *A61P 9/00* | (2006.01) | |
| *A61P 13/12* | (2006.01) | |
| *A61P 11/00* | (2006.01) | |
| *A61K 31/192* | (2006.01) | |

(52) U.S. Cl.
CPC ........ *A61K 31/4375* (2013.01); *A61K 31/167* (2013.01); *A61K 31/192* (2013.01); *A61K 31/4365* (2013.01); *A61K 45/06* (2013.01); *A61P 9/00* (2018.01); *A61P 11/00* (2018.01); *A61P 13/12* (2018.01)

(58) Field of Classification Search
CPC ..... C07D 471/04; A61K 31/4375; A61P 9/00; A61P 9/04; A61P 9/12
USPC .................. 546/122; 514/300, 578; 562/512
See application file for complete search history.

(56) References Cited

U.S. PATENT DOCUMENTS

| | | | |
|---|---|---|---|
| 8,420,656 B2 | 4/2013 | Follmann et al. | |
| 8,436,180 B2* | 5/2013 | Barfacker ............ | C07D 471/04 |
| | | | 546/122 |
| 8,796,335 B2* | 8/2014 | Hahn ...................... | A61P 13/12 |
| | | | 514/563 |
| 9,051,316 B2 | 6/2015 | Barfacker et al. | |
| 10,023,528 B2 | 7/2018 | Hahn et al. | |
| 10,259,776 B2 | 4/2019 | Hahn et al. | |
| 10,905,667 B2 | 2/2021 | Stroyer et al. | |
| 2015/0126501 A1 | 5/2015 | Huang et al. | |
| 2020/0237648 A1 | 7/2020 | Stroyer et al. | |
| 2020/0385335 A1 | 12/2020 | Hahn et al. | |

FOREIGN PATENT DOCUMENTS

| | | |
|---|---|---|
| DE | 102007009494 A1 | 8/2008 |
| DE | 102010021637 A1 | 12/2011 |
| DE | 102011007272 A1 | 10/2012 |
| EP | 3498298 A1 | 6/2019 |
| WO | 9816223 A1 | 4/1998 |
| WO | 9816507 A2 | 4/1998 |
| WO | 9823619 A1 | 6/1998 |
| WO | 0006568 A1 | 2/2000 |
| WO | 0006569 A1 | 2/2000 |
| WO | 0236120 A1 | 5/2002 |
| WO | 0242299 A1 | 5/2002 |
| WO | 0242300 A1 | 5/2002 |
| WO | 0242301 A1 | 5/2002 |
| WO | 0242302 A1 | 5/2002 |
| WO | 02070461 A1 | 9/2002 |
| WO | 02092596 A1 | 11/2002 |
| WO | 03004503 A1 | 1/2003 |
| WO | 03095451 A1 | 11/2003 |
| WO | 03097063 A1 | 11/2003 |

(Continued)

OTHER PUBLICATIONS

Bell M.G. et al., "(S)—N-{3-1-Cyclopropryl1-1-(2,4-difluoro-phenyl)-ethyl]-1H-indol-7-yl}-methanesulfonamide: A Potent, Nonsteroidal, Functional Antagonist of the Mineralocorticoid Receptor," Journal of Medicinal Chemistry, 2007; 50:6443-6445.

Conti and Beaver et al.; "Biochemistry and Physiology of Cyclic Nucleotide Phosphodiesterases: Essential Components in Cyclic Nucleotide Signaling;" Annu. Rev. Biochem., 2007, 76, pp. 481-511.

Casimiro-Garcia, A. et al., "Identification of (R)-6-(1-(4-Cyano-3-methylphenyl)-5-cyclopentyl-4,5-dihydro-1H-pyrazol-3-yl)-2-methoxynicotinic Acid, a Highly Potent and Selective Nonsteroidal Mineralocorticoid Receptor Antagonist;" Journal of Medicinal Chemistry, 2014, 57, pp. 4273-4285.

(Continued)

*Primary Examiner* — Charanjit Aulakh
(74) *Attorney, Agent, or Firm* — Quarles & Brady LLP

(57) ABSTRACT

The present invention relates to the combination of activators of soluble guanylate cyclase (sGC activators) with mineralocorticoid receptor antagonists (MR antagonists) and to the use of the combination for the treatment and/or prophylaxis of cardiac and cardiovascular disorders, of renal and cardiorenal disorders, of pulmonary and cardiopulmonary disorders and also for the treatment and/or prophylaxis of fibrotic disorders.

13 Claims, No Drawings

(56) References Cited

FOREIGN PATENT DOCUMENTS

| | | |
|---|---|---|
| WO | 2004009589 A1 | 1/2004 |
| WO | 2005042022 A2 | 5/2005 |
| WO | 2006012642 A2 | 2/2006 |
| WO | 2007089034 A1 | 8/2007 |
| WO | 2007124854 A1 | 11/2007 |
| WO | 2008031513 A1 | 3/2008 |
| WO | 2008061657 A1 | 5/2008 |
| WO | 2008104306 A2 | 9/2008 |
| WO | 2010065275 A1 | 6/2010 |
| WO | 2010079120 A1 | 7/2010 |
| WO | 2010102717 A1 | 9/2010 |
| WO | 2011115804 A1 | 9/2011 |
| WO | 2011119518 A1 | 9/2011 |
| WO | 2011147809 A1 | 12/2011 |
| WO | 2011149921 A1 | 12/2011 |
| WO | 2011161099 A1 | 12/2011 |
| WO | 2012003405 A1 | 1/2012 |
| WO | 2012004258 A1 | 1/2012 |
| WO | 2012004259 A1 | 1/2012 |
| WO | 2012028647 A1 | 3/2012 |
| WO | 2012059548 A1 | 5/2012 |
| WO | 2012059549 A1 | 5/2012 |
| WO | 2012064559 A1 | 5/2012 |
| WO | 2012097744 A1 | 7/2012 |
| WO | 2012139495 A1 | 10/2012 |
| WO | 2012143510 A1 | 10/2012 |
| WO | 2012152629 A1 | 11/2012 |
| WO | 2012152630 A1 | 11/2012 |
| WO | 2012165399 A1 | 12/2012 |
| WO | 2013004785 A1 | 1/2013 |
| WO | 2013030288 A1 | 3/2013 |
| WO | 2013055606 A1 | 4/2013 |
| WO | 2013055607 A1 | 4/2013 |
| WO | 2013055608 A1 | 4/2013 |
| WO | 2013101830 A1 | 7/2013 |
| WO | 2013104597 A1 | 7/2013 |
| WO | 2013104598 A2 | 7/2013 |
| WO | 2013104703 A1 | 7/2013 |
| WO | 2013131923 A1 | 9/2013 |
| WO | 2014014794 A2 | 1/2014 |
| WO | 2014047111 A1 | 3/2014 |
| WO | 2014047325 A1 | 3/2014 |
| WO | 2014068095 A1 | 5/2014 |
| WO | 2014068099 A1 | 5/2014 |
| WO | 2014068104 A1 | 5/2014 |
| WO | 2014084312 A1 | 6/2014 |
| WO | 2014128109 A1 | 8/2014 |
| WO | 2014131741 A1 | 9/2014 |
| WO | 2014131760 A1 | 9/2014 |
| WO | 2014144100 A2 | 9/2014 |
| WO | 2014195333 A1 | 12/2014 |
| WO | 2015004105 A1 | 1/2015 |
| WO | 2015018808 A1 | 2/2015 |
| WO | 2015018814 A1 | 2/2015 |
| WO | 2015088885 A1 | 6/2015 |
| WO | 2015088886 A1 | 6/2015 |
| WO | 2015089182 A1 | 6/2015 |
| WO | 2015187470 A1 | 12/2015 |
| WO | 2016044441 A1 | 3/2016 |
| WO | 2016044446 A2 | 3/2016 |
| WO | 2016044447 A1 | 3/2016 |
| WO | 2016081668 A1 | 5/2016 |
| WO | 2019/211081 A1 | 11/2019 |

OTHER PUBLICATIONS

Cox J.M. et al., "Mineralocorticoid receptor antagonists: Identification of heterocyclic amide replacements in the oxazolidinedione series," Bioorg Med Chem Lett 2014; 24: pp. 1681-1684.

Derbyshire E.R. and Marietta M.A., "Structure and Regulation of Soluble Guanylate Cyclase," Annu. Rev. Biochem., 2012, vol. 81, pp. 533-559.

Evgenov O.V. et al., "NO-independent stimulators and activators of soluble guanylate cyclase: discovery and therapeutic potential," Nat. Rev. Drug Discov., 2006 5(9), pp. 755-768.

Futatsugi K. et al., "Design and synthesis of aryl sulfonamide-based nonsteroidal mineralocorticoid receptor antagonists," Bioorganic & Medicinal Chemistry Letters, vol. 23, No. 23, 2013, 6239-6242.

Ghofrani et al. (A), "Riociguat for the Treatment of Chronic Thromboembolic Pulmonary Hypertension," New Engl. J. Med., 2013, 369, pp. 319-329.

Ghofrani et al. (B), "Riociguat for the Treatment of Pulmonary Arterial Hypertension," New Engl. J. Med., 2013, vol. 369, pp. 330-340.

Gheorghiade M. et al., "Effect of Vericiguat, a Soluble Guanylate Cyclase Stimulator, on Natriuretic Peptide Levels in Patients With Worsening Chronic Heart Failure and Reduced Ejection Fraction, The Socrates-Reduced Randomized Trial," JAMA, 31(21), 2015, pp. 2251-2262.

Hambly N. & Granton J., "Riociguat for the treatment of pulmonary hypertension," Expert Review of Respiratory Medicine, 9(6), 2015, pp. 679-695.

McKelvie, R.S. et al., "Comparison of Candesartan, Enalapril, and Their Combination in Congestive Heart Failure," Circulation, 1999, 100, pp. 1056-1064.

Meyers, M.J. et al., "Discovery of (3S,3aR)-2-(3-Chloro-4-cyanophenyl)-3,3a,4,5-tetrahydro-2H-benzo[g]indazole-7-carboxylic Acid (PF-3882845), an Orally Efficacious Mineralocorticoid Receptor (MR) Antagonist for Hypertensions and Nephropathy," J. Med. Chem., 2010, 53, pp. 5979-6002.

Neel D.A. et al., "3,3-Bisaryloxindoles as mineralocorticoid receptor antagonists," Bioorganic & Medicinal Chemistry Letters, 2005, vol. 15, pp. 2553-2557.

Monica F.Z. et al., "The Endothelium—Dependent Nitric Oxide—cGMP Pathway," Advances in Pharmacology, vol. 77, 2016, pp. 1-27.

Pieskie B. et al., "Rationale and design of the SOluble guanylate Cyclase stimulatoR in HeArT failurE Studies (SOCRATES)," European Journal of Heart Failure, 2014, 16, pp. 1016-1038.

Schmidt et al. (Eds.), "cGMP: Generators, Effectors and Therapeutic Implications," Stasch & Hobbs, Handbook of Experimental Pharmacology, 2009, 191, pp. 277-308.

Stasch et al. (A) and (B), "NO-independent regulatory site on soluble guanylate cyclase," Nature, vol. 410, 2001, pp. 212-215.

Stasch et al., "Soluble Guanylate Cyclase as an Emerging Therapeutic Target in Cardiopulmonary Disease," Circulation—Review, Journal American Heart Assoc., 2011, 123, pp. 2263-2273.

Stasch and Hobbs, "cGMP: Generators, Effectors and Therapeutic Implications." Handbook of Experimental Pharmacology 191, 2009, pp. 227-308.

Yang C. et al., "Discovery of Benzimidazole Oxazolidinediones as Novel and Selective Nonsteroidal Mineralocorticoid Receptor Antagonists," ACS Medicinal Chemistry Letters, 2015, 6, pp. 461-465.

Yang C. et al., "Discovery of novel oxazolidinedione derivatives as potent and selective mineralocorticoid receptor antagonists," Bioorganic & Medicinal Chemistry Letters, 2013, 23, pp. 4388-4392.

Hao A. Tran et al., "Potential new drug treatments for congestive heart failure," Expert Opinion on Investigational Drugs, Bd. 25, No. 7, 2016, pp. 811-826.

Harald H.H.W. Schmidt et al., NO- and Haem-Independent Soluble Guanylate Cyclase Activators, Handbook of Experimental Pharmacology 191, copyright date 2009, pp. 309-338, Springer-Verlag Berlin Heidelberg.

F. Jaisser and N. Farman, Emerging Roles of the Mineralocorticoid Receptor in Pathology: Toward New Paradigms in Clinical Pharmacology, Pharmacological Reviews, Jan. 2016, pp. 49-75, The American Society for Pharmacology and Experimental Therapeutics.

Kolkhoff P. et al., "Nonsteroidal Antagonists of the Mineralocorticoid Receptor," Curr Opin Nephrol Hypertens 2015, vol. 24, No. 5, pp. 417-424.

Kolkhoff P. et al., "Mineralocorticoid Receptor Antagonists: 60 Years of Research and Development," Journal of Endocrinology 2017, vol. 234, pp. T125-T140.

(56) References Cited

OTHER PUBLICATIONS

Sandner P. et al., "Soluble Guanylate Cyclase Stimulators and Activators, in Handbook of Experimental Pharmacology," Jan. 29, 2019, Pub.: Springer Verlag; Berlin and Heidelberg, Germany.

Engler et al.,"The TGR(mRen2)27 Transgenic Rat Model of Hypertension," Regulatory Peptides 1998;77:3-8.

Mullins et al., "Renal Disease Pathophysiology and Treatment: Contributions from the Rat," Disease Models & Mechanisms 2016;9:1419-1433.

Kovacs et al., "Renin Overexpression Leads to Increased Titin-Based Stiffness Contributing to Diastolic Dysfunction in Hypertensive mRen2 Rats," Am J Physiol Heart Circ Physiol 2016;310: H1671-H1682.

Messerli et al., "Essential Hypertension," Lancet 2007; 370: 591-603.

Mullins et al., "Fulminant Hypertension in Transgenic Rats Harbouring the Mouse Ren-2 Gene," Nature 1990, 344 (6266), pp. 541-544.

\* cited by examiner

COMBINATION CONTAINING SGC ACTIVATORS AND MINERALOCORTICOID RECEPTOR ANTAGONISTS

This application is the U.S. national stage entry under 35 U.S.C. 371 of PCT Application No. PCT/EP2017/075356 filed on Oct. 5, 2017, which is hereby incorporated herein in its entirety, which claims priority to European Application No. 16193367.6, filed Oct. 11, 2016.

The present invention relates to the combination of activators of soluble guanylate cyclase (sGC activators) with mineralocorticoid receptor antagonists (MR antagonists) and to the use of the combination for the treatment and/or prophylaxis of cardiac and cardiovascular disorders, of renal and cardiorenal disorders, of pulmonary and cardiopulmonary disorders and also for the treatment and/or prophylaxis of fibrotic disorders.

The entire body function of humans and animals is controlled and maintained by regulatory circuits. For their part, these physiological regulatory circuits comprise cascade systems of endogenous hormones, enzymes and receptors. These regulatory circuits are linked to one another and centrally controlled. Pathophysiological changes in the body, but also external effects such as climate, stress, food components including medicaments, have a direct effect on these regulatory circuits. Reduced or excessive activities of individual components of these cascades and regulatory systems can be compensated by counteracting by means of feed-back or else feed-forward mechanisms. Short-term counteracting, e.g. by compensatory release of a certain endogenous hormone, is thus vital for maintenance of body function in emergency situations (e.g. in the case of injuries). However, long-term, permanent compensatory counterregulation may also have fatal consequences for the entire organism.

Most therapeutic approaches for treating disorders of the cardiac and cardiovascular system, the renal and cardiorenal system or the pulmonary and cardiopulmonary system and fibrotic disorders intervene in one of the regulatory systems mentioned. This may be associated with the disadvantage that, owing to compensatory counterregulation of the body, there is desensitization even after a short time, and the desired effect is no longer obtained, or reduced, thus requiring the use of higher dosages, inter alia. This is associated with disadvantages such as a higher risk of side-effects.

It is the object of the present invention to provide combinations of pharmaceutically active substances which act on more than one regulatory circuit and which can be employed for the treatment of cardiac and cardiovascular disorders, of renal and cardiorenal disorders, of pulmonary and cardiopulmonary disorders and fibrotic disorders.

One of these essential regulatory systems mentioned above is the renin angiotensin aldosterone system (RAAS). This is a central cascade system of hormones and enzymes which control salt and water balance and thus the blood pressure of the body. In cases of lack of salt and fluid or a drop in blood pressure, the hormone renin is formed in and secreted by special kidney cells. Renin cleaves angiotensinogen, which is formed in the liver, to angiotensin I, whereas the angiotensin conversion enzyme (ACE) transforms angiotensin I into angiotensin II. Angiotensin II has potent vasoconstrictive and thus hypertensive effects and stimulates the formation of the steroid hormone aldosterone in the adrenal cortex. Aldosterone promotes the re-uptake of sodium from the urine into the blood, which increases blood volume.

The specific effects of angiotensin II are mediated by corresponding extracellular receptors (angiotensin receptor, AT-R) which are expressed on target cells of the cardiovascular system. In contrast, the specific effects of aldosterone are mediated via an intracellular receptor, the aldosterone or mineralocorticoid receptor (MR). In addition to their central importance in salt, water and blood pressure regulation, both angiotensin II and aldosterone have direct pro-inflammatory and pro-fibrotic properties. Both hormones play an essential role, in particular in the 'remodeling' of heart, kidneys and vessels induced, for example, by myocardial infarction or acute kidney failure: thus, for example, aldosterone stimulates the storage of collagen proteins in the heart muscle, which may result in increased stiffness and therefore reduced functionality long-term.

Aldosterone and angiotensin II form a classic feed-forward regulatory circuit: In addition to potassium, angiotensin II is the most important stimulus for the release of aldosterone from the adrenal gland, and conversely aldosterone in heart tissue and blood vessels stimulates the production of ACE, i.e. the enzyme which generates, from the precursor angiotensin, angiotensin II.

The pathophysiological effects of angiotensin II and aldosterone can be reduced by appropriate inhibitors of ACE, the AT-R and the MR; however, these singular blockades are subject to the above-mentioned feed-back compensation mechanisms, i.e. a blockade of the mineralocorticoid receptors leads to compensatory release of aldosterone, similar to how an AT-R blockade leads to an increase of angiotensin II.

Long-term compensatory mechanisms play a special role in the clinically relevant 'aldosterone escape' phenomenon: Since the release of aldosterone represents the last step in the RAAS cascade, it has been believed for a long time that the blockade of the initial RAAS key steps such as ACE activity or the AT-R would be sufficient to also prevent the last step, i.e. aldosterone formation and release in the adrenal gland. However, the RESOLVD study (McKelvie et al., Circulation 1999; 100; 1056-1064) found that both under singular ACE or AT-R blockade and under dual ACE/AT-R blockade the aldosterone plasma levels in patients with heart failure are reduced compared to baseline for the first 17 weeks of treatment, but after 43 weeks baseline is even exceeded. The results of this study confirm that prevention of binding of aldosterone to the mineralocorticoid receptor in addition to the angiotensin blockade is of enormous clinical relevance.

MR antagonists (such as the steroidal compounds spironolactone, canrenone/canrenoate and eplerenone, and also more recent non-steroidal MR antagonists such as MT-3995 according to the compound of the formula (VI), CS-3150 according to the compound of the formula (V), LY2623091, PF-03882845 according to the compound of the formula (XIV) and finerenone, according to the compound of the formula (IV)) counteract aldosterone-mediated sodium retention in the kidneys (natriuretic effect). Thus, MR antagonists lead to increased sodium excretion, which is a proven therapeutic concept for hypertensive patients and/or patients suffering from heart failure and/or kidney failure. However, MR antagonists can unfold their natriuretic action only in kidney segments in which aldosterone also exerts its physiological action via the MR. These are in particular the late distal tubulus and collecting duct sections involved in sodium re-resorption only to a limited extent, whereas most of sodium secretion and re-resorption takes place in proximal tubulus sections.

However, in addition to the RAAS there are also other very important regulatory systems, one of them being the nitric oxide (NO) cyclic guanosine monophosphate (cGMP) and phosphodiesterase (PDE) signalling pathway (NO/cGMP path). An increase in blood pressure and the resulting shear forces on the endothelial cells in blood vessels leads to enzymes in endothelial cells, but also in nerve endings, i.e. NO synthases (NOS) forming NO from L-arginine. This NO is gaseous and diffuses through the cell membranes into various target cells, in particular into cells of the vascular musculature. There, it binds to the haem group in soluble guanylate cyclase (sGC), a heterodimeric intracellular haem protein consisting of an alpha and a beta subunit. NO bindung activates the enzyme, which then catalyses the transformation of guanosine triphosphate (GTP) into cGMP. This cGMP is an important second messenger molecule and binds to a large number of intracellular proteins, among others cGMP-dependent protein kinases (G kinases). Via phosphorylation of various target proteins, e.g. potassium channels, G kinases mediate lowering of the intracellular calcium concentration, which triggers relaxation of the vascular musculature, for example. Accordingly, via stimulation of the sGC/cGMP path, NO has vasodilatory and thus hypotensive action. In addition, numerous other actions of cGMP have also been described, such as, for example, antithrombotic, antifibrotic or anti-inflammatory action. However, on a molecular level these actions are less well understood than vasodilation, and they have not yet been elucidated completely. NO/cGMP signal cascade and the actions of cGMP are terminated by degradation of cGMP to ineffective GMP. This step, the hydrolysis of the cyclic phosphate ring and the formation of 5'GMP, is catalysed by phosphodiesterases (PDE). The PDEs are a large family of enzymes of currently eleven identified members and more than 100 different splicing variants. The different PDEs differ mainly with respect to tissue specificity (PDE6, for example, is expressed exclusively in the eye), substrate specificity (e.g. cAMP- or cGMP-specific) and regulation (e.g. via calcium/calmodulin or cyclic nucleotides). Specific cleavage of cGMP is effected mainly by PDEs of type 5 (PDE5), 6 (PDE6) and 9 (PDE9). (cf. reviews about the NO/cGMP/PDE signalling pathway, e.g. Conti & Beavo 2007, Schmidt et al. (editors) 2009; Stasch et al. 2011, Derbyshire and Marietta 2012, Monica et al. 2016).

With a view to the great importance of the NO/cGMP signalling pathway for physiological regulation and maintenance of body functions, in particular for the function of the cardiac and cardiovascular system, the vascular system, kidney function or the lungs and cardiopulmonary function, but also of antifibrotic effects, a number of pharmaceuticals which intervene at various important switching points in this signalling pathway have been investigated and developed. This was all the more necessary since it is known that various disorders of the organ systems mentioned above are associated with reduced NO formation, which leads to an inadequate cGMP supply and could be one of the underlying pathomechanisms in the development of cardiac and cardiovascular, renal, pulmonary and fibrotic disorders.

For example, the use of nitrates and NO donors in the treatment of angina pectoris, both for suppressing acute episodes and for the prophylaxis of episodes has been known for a long time. Enzymatically or non-enzymatically, these compounds released NO which can then bind to sGC, leading to elevated cGMP concentrations. However, in addition to the kinetic limitations of these compounds, it is mainly an increased formation of free radicals with potential vessel- and organ-damaging effects and the development of tachyphylaxia which limit the therapeutic potential significantly.

Accordingly, more recent developments were focused inter alia on inhibiting cGMP degradation by inhibiting specific PDEs, in particular inhibiting PDE5. The development of potent and selective PDE5 inhibitors such as, for example, sildenafil, vardenafil or tadalafil, once more demonstrated the effectiveness of this signalling pathway for regulating vascular tone. This was followed by clinical approval of preparations for the treatment of erectile dysfunction (ED), of pulmonary arterial hypertension (PAH) and of benign prostate hyperaplasia (BPH). Moreover, these compounds are also clinically trialled for use for cardiac and cardiovascular disorders and for renal disorders. Again, this demonstrates the ubiquitous significance of this NO/cGMP signalling pathway and underlines the broad application potential of these cGMP-elevating compounds. However, treatment options with PDE5 inhibitors are limited as they require a sufficiently high endogenous cGMP concentration in order to be active which is then protected against degradation by the compounds. In the case of many disorders including in particular cardiac and cardiovascular disorders or lung disorders, however, endogenous NO production and thus also cGMP formation is at least partially impaired. This is why PDE5 inhibitors are not equally effective in all patients and why there are also treatment-resistant patients, e.g. in cases of erectile dysfunction or pulmonary hypertension.

To overcome this limitation of both nitrates and PDE5 inhibitors, there have been attempts of direct pharmacological stimulation of sGC. Firstly, this is to avoid the NO-dependent free-radical formation of the nitrates, but secondly, this is also to avoid dependence of the efficacy on the cGMP produced, as described for PDE5 inhibitors. Accordingly, investigation and development of sGC stimulators and sGC activators represents a milestone in the pharmacology of the NO/cGMP signalling path. These two compound classes, sGC stimulators and sGC activators, stimulate sGC independently of NO and lead to an NO-independent production of cGMP. In addition, however, these compound classes also act synergistically (sGC stimulators) and additively (sGC activators) to endogenously formed NO. As far as is currently known, the main difference is sGC binding. sGC is a heterodimeric protein formed by an alpha and a beta subunit; the latter carries the NO-binding haem group. The sGC stimulators bind to the alpha subunit of non-oxidized and haem-containing sGC and cause direct NO-independent formation of cGMP (Stasch et al. (A) 2001; Stasch & Hobbs 2009). In contrast, the sGC activators bind to the beta subunit of oxidized and haem-free sGC, activating it, and thus leading to NO-independent formation of cGMP (Stasch et al. (B) 2001, Schmidt et al. 2009). This principal difference is very well established for in vitro conditions; however, understanding of the physiological and pathophysiological consequences of the presence of haem-containing and oxidized haem-free sGC and the resulting treatment potential of these compound classes is still incomplete. Nevertheless, the pharmacological utility of sGC stimulators and sGC activators has been demonstrated in numerous preclinical models and for numerous different indications, in particular in the field of cardiac and cardiovascular disorders, of renal and cardiorenal disorders, of pulmonary and cardiopulmonary disorders (Evgenov et al. 2009, Stasch et al. 2011). This was also confirmed in clinical studies, and accordingly in 2013 the sGC stimulator riociguat was approved for the treatment of pulmonary arterial hypertension (PAH) and of chronic thromboembolic pulmonary hypertension (CTEPH) (Ghofrani et al. (A), Ghofrani et al. (B) 2013, 2013 Hambly & Granton 2015). In addition, the sGC stimulator vericiguat is in phase I/III for the treatment of heart failure (Pieske et al. 2014, Gheorghiade et al. 2015). These examples also confirm clinically the broad possible use of sGC stimulators and sGC activators in the field of treatment and/or prophylaxis of cardiac and cardiovascular disorders, of renal and cardiorenal disorders and of pulmonary and cardiopulmonary disorders. Moreover, preclinically, antifibrotic action of sGC stimulators and sGC activators was demonstrated convincingly.

In principle, a distinction is made between MR antagonists (MRAs) having a steroidal skeleton and those having a non-steroidal skeleton. Steroidal MRAs such as spironolactone or its active metabolite kanrenone interact not only with the MR, but also with the homologous androgen and progesterone receptors. These interactions may result in unwanted effects on sexual hormone metabolism such as gynecomasty, dysmenorrhoea and loss of libido. Non-steroidal MRAs such as finerenone interact specifically with the MR, so corresponding side-effects possibly resulting from interactions with other steroid hormone receptors are not to be expected.

Examples of steroidal mineralocorticoid receptor antagonists are (the subject-matter disclosed in the publications below with respect to the steroidal MR antagonists hereby also forms part of the subject-matter of the disclosure of the present application)

spironolactone (7α-acetylthio-3-oxo-17α-pregn-4-ene-21,17β-carbolacto-7α-acetylthio-3-oxo-17α-pregn-4-ene-21,17β-carbolactone) of the formula (I)

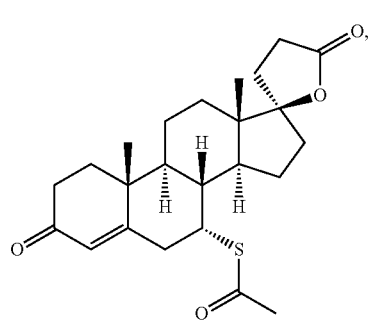

which is known from the literature and is already commercially available as a medicament, among others under the tradenames Aldactone, Jenasprion, Asyrol, Spirobene, Verospiron, Xenalon, eplerenone (epoxymexerenone) of the formula (II)

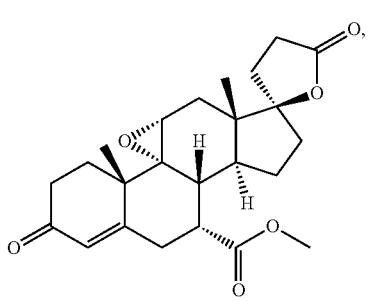

which is known from the literature and is already commercially available as a medicament, among others under the tradename Inspra, kanrenone (10,13-dimethylspiro[2,8,9,11,12,14,15,16-octahydro-1H-cyclopenta[a]phenanthrene-17,5'-oxolane]-2',3-dione) of the formula (III)

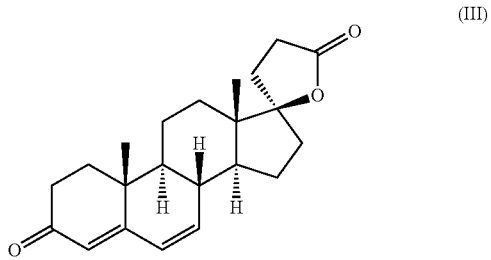

which is an active metabolite of spironolactone, is known from the literature and is already commercially available as a medicament, among others under the tradenames Contaren, Luvion and Phanurane. Kanrenone is also known and commercially available as the potassium salt potassium kanrenoate.

Examples of non-steroidal mineralocorticoid receptor antagonists are (the subject-matter disclosed in the publications below with respect to the non-steroidal MR antagonists hereby also forms part of the subject-matter of the disclosure of the present application):

finereneone ((S)-4-(4-cyano-2-methoxyphenyl)-5-ethoxy-2,8-dimethyl-1,4-dihydro-1,6-naphthyridine-3-carboxamide), as a selective antagonist, based on a dihydropyridine skeleton, of the formula (IV)

which is described in DE 10 2007009494 A1 and WO 2008 104 306 A2, esaxerenone (1-(2-hydroxyethyl)-4-methyl-N-(4-(methylsulfonyl)phenyl)-5-(2-(trifluoromethyl) phenyl)-1H-pyrrole-3-carboxamide) of the formula (V)

which is disclosed in WO2006/012642, apararenone (N-(4-(4-fluorophenyl)-2,2-dimethyl-3-oxo-3,4-dihydro-2H-benzo[b][1,4]oxazin-7-yl)methanesulfonamide) of the formula (VI)

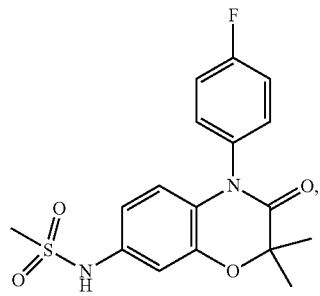

(VI)

which is disclosed in WO07/089034,

PF-03882845 ((3S,3aR)-2-(3-chloro-4-cyanophenyl)-3-cyclopentyl-3,3a,4,5-tetrahydro-2H-benzo[g]indazole-7-carboxylic acid) of the formula (XIV)

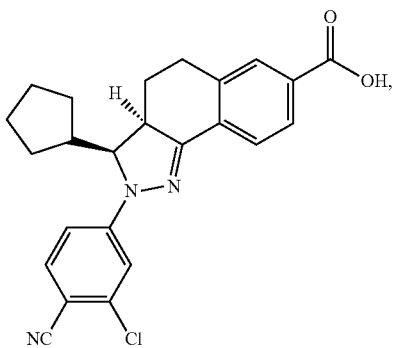

(XIV)

which is disclosed in the following publications:

Meyers, M. J, Arhancet, G. B., Hockerman, S. L., Chen, X., Long, S. A., Mahoney, M. W., Rico, J. R., Garland, D. J., Blinn, J. R., Collins, J. T., Yang, S., Huang, H. C., McGee, K. F., Wendling, J. M., Dietz, J. D., Payne, M. A., Homer, B. L., Heron, M. I., Reitz, D. B., Hu, X., 2010. Discovery of (3S, 3aR)-2-(3-chloro-4-cyanophenyl)-3-cyclopentyl-3, 3a, 4, 5-tetrahydro-2H-benzo[g]indazole-7-carboxylic acid (PF-3882845), an orally efficacious mineralocorticoid receptor (MR) antagonist for hypertension and nephropathy. J. Med. Chem. 53, 5979-6002, (R)-6-(1-(4-cyano-3-methylphenyl)-5-cyclopentyl-4,5-dihydro-1H-pyrazol-3-yl)-2-methoxynicotinic acid of the formula (VIII)

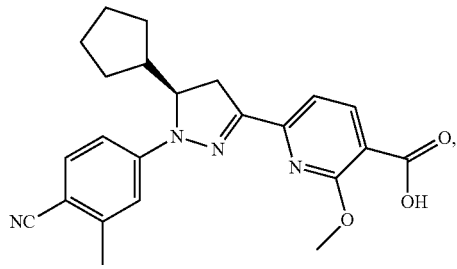

(VIII)

which is disclosed in the following publications:

Casimiro-Garcia A, Piotrowski D W, Ambler C, et al. Identification of (R)-6-(1-(4-cyano-3-methylphenyl)-5-cyclopentyl-4,5-dihydro-1H-pyrazol-3-yl)-2-methoxynicotinic acid, a highly potent and selective nonsteroidal mineralocorticoid receptor antagonist. J Med Chem 2014; 57:4273-4288, MR antagonists based on an arylsulfonamide structure, such as those disclosed in Futatsugi K, Piotrowski D W, Casimiro-Garcia A, et al. Design and synthesis of aryl sulfonamide-based nonsteroidal mineralocorticoid receptor antagonists. Bioorg Med Chem Lett 2013; 23:6239-6242, KBP-5074, which is disclosed in US2015/0126501, (S)—N-{3-[1-cyclopropyl-1-(2,4-difluorophenyl)ethyl]-1H-indol-7-yl}methanesulfonamide, which is based on an indole skeleton, of the formula (IX)

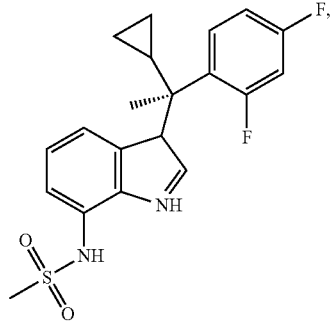

(IX)

which is disclosed in the following publications:

Bell M G, Gernert D L, Grese T A, Belvo M D, Borromeo P S, Kelley S A, Kennedy J H, Kolis S P, Lander P A, Richey R, Sharp V S, Stephenson G A, Williams J D, Yu H, Zimmerman K M, Steinberg M I, Jadhav P K. (S)—N-{3-[1-cyclopropyl-1-(2,4-difluoro-phenyl)-ethyl]-1H-indol-7-yl}-methanesulfonamide: a potent, nonsteroidal, functional antagonist of the mineralocorticoid receptor. J Med Chem. 2007; 50:6443-6445.

Bisaryloxinidoles, which are disclosed in Neel D A, Brown M L, Lander P A, Grese T A, Defauw J M, Doti R A, Fields T, Kelley S A, Smith S, Zimmerman K M, Steinberg M I, Jadhav P K. 3,3-Bisaryloxindoles as mineralocorticoid receptor antagonists. Bioorg Med Chem Lett. 2005; 15:2553-2557, and also MR antagonists based on an oxazolidinedione skeleton, which are disclosed in the following publications:

Yang C, Shen H C, Wu Z, et al. Discovery of novel oxazolidinedione derivatives as potent and selective mineralocorticoid receptor antagonists. Bioorg Med Chem Lett 2013; 23:4388-4392. Cox J M, Chu H D, Yang C, et al. Mineralocorticoid receptor antagonists: identification of heterocyclic amide replacements in the oxazolidinedione series. Bioorg Med Chem Lett 2014; 24:1681-1684. Yang C, Balsells J, Chu H D, Cox J M, Crespo A, Ma X, Contino L, Brown P, Gao S, Zamlynny B, Wiltsie J, Clemas J, Lisnock J, Gibson J, Zhou G, Garcia-Calvo M, Bateman T J, Tong V, Xu L, Crook M, Sinclair P, Shen H C. Discovery of benzimidazole oxazolidinediones as novel and selective nonsteroidal mineralocorticoid receptor antagonists. ACS Med Chem Lett. 2015; 6:461-465, mineralocorticoid receptor antagonists based on an indole or indazole skeleton, as disclosed in WO2012/097744, WO2013055606, WO2013055607, WO2013055608, WO2014014794, WO2012139495.

Suitable sGC activators are known from the following publications (the subject-matter disclosed in the publications below hereby also forms part of the subject-matter of the disclosure of the present application):

WO2013/157528, WO2015/056663, WO2009/123316, WO2016/001875, WO2016/001876, WO2016/001878, WO2000/02851, WO2012/122340, WO2013/025425, WO2014/039434, WO2016/014463, WO2009/068652, WO2009/071504, WO2010/015652, WO2010/015653, WO2015/033307, WO2016/042536, WO2009/032249, WO2010/099054, WO2012/058132, US2010/0216764, WO01/19776, WO01/19780, WO01/19778, WO02/070459, WO02/070460, WO02/070510, WO02/070462, WO2007/045366, WO2007/045369, WO2007/045433, WO2007/045370, WO2007/045367, WO2014/012935, WO2014/012934, WO2011/141409, WO2008/119457, WO2008/119458, WO2009/127338, WO2010/102717, WO2011/051165, WO2012/076466, WO2012/139888, WO2013/174736.

The following sGC activators are of particular importance:

(3S)-3-(4-chloro-3-{[(2S,3R)-2-(4-chlorophenyl)-4,4,4-trifluoro-3-methylbutanoyl]amino}phenyl)-3-cyclopropyl-propanoic acid of the formula (X)

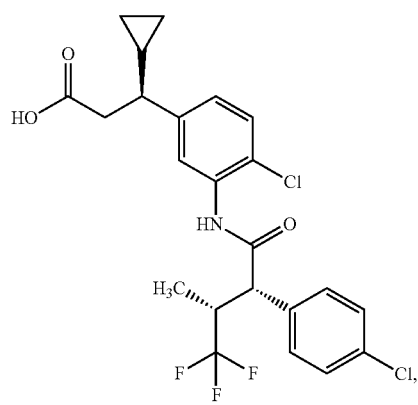

(X)

which is disclosed in WO2012/139888, 4-({(4-carboxybutyl)[2-(2-{[4-(2-phenylethyl)benzyl]oxy}phenyl)ethyl]amino}methyl)carboxylic acid of the formula (XI)

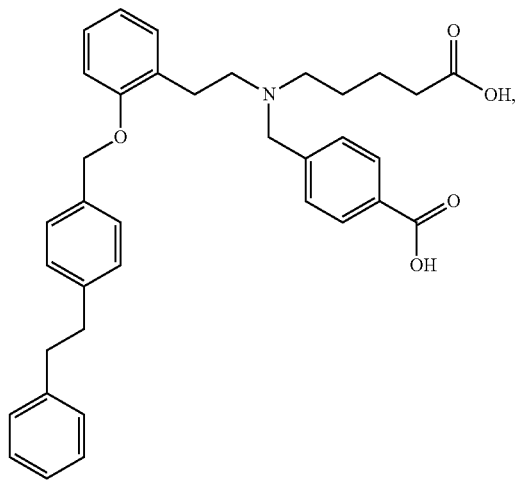

(XI)

which is disclosed in WO 01/019780,

5-{(4-carboxybutyl)[2-(2-{[3-chloro-4'-(trifluoromethyl)biphenyl-4-yl]methoxy}phenyl)ethyl]amino}-5,6,7,8-tetrahydroquinoline-2-carboxylic acid of the formula (XII)

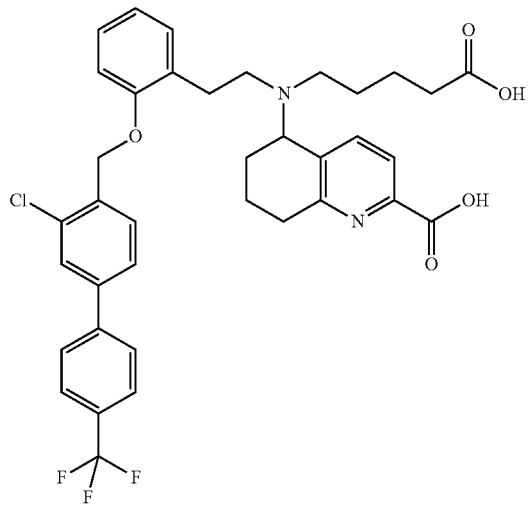

(XII)

which is disclosed in WO2014/012934,

5-{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid of the formula (XIII)

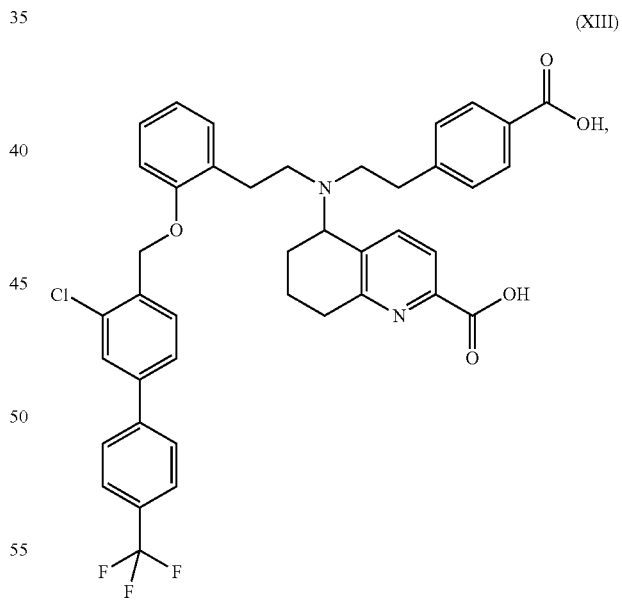

(XIII)

which is disclosed in WO2014/012934, and the sGC activator BI 703704 which is in clinical development by Boehringer Ingelheim, and also other sGC activators in preclinical research and development.

Both the RAAS and the NO/cGMP route play an important role in maintaining homeostasis of the body and regulate important functions in the cardiac and cardiovascular system, in the renal and cardiorenal system or in the pulmonary and cardiopulmonary system. The use of MR antagonists and the use of sGC activators as monotherapies for cardiac and cardiovascular disorders, for renal and cardiorenal disorders, for pulmonary and cardiopulmonary disorders or for fibrotic disorders has also been described. However, in actual fact both the proportion of the dysregulation of the two signal paths in these different disorders and the absolute efficiency of the two mechanisms in direct comparison are unknown.

Accordingly, experiments were carried out where sGC activators were compared directly with MR antagonists. This was done in order to gain an insight into qualitative and quantitative disease relevance of these two pathomechanisms and to research the treatment paradigms derivable therefrom.

In these experiments, combinations of MR antagonists and sGC activators were employed and also tested in direct comparison with the individual compounds. Surprisingly, an exceptional efficacy of these combinations was found which exceeded the efficacy of the individual components by far and which suggests a synergistic activity of the combination of MR antagonists and sGC activators.

The solution to the object defined above may therefore consist in the provision of combinations comprising at least one sGC activator and at least one substance which intervenes in the RAAS system, and being able to be used for the targeted treatment of cardiac and cardiovascular disorders, renal and cardiorenal disorders, pulmonary and cardiopulmonary disorders and fibrotic disorders, with super-additive effects.

Accordingly, the invention provides inter alia a combination comprising MR antagonists and sGC activators. When used under acute and in particular under chronic conditions, the combination displays positive effects with respect to end organ protection of heart and kidneys, reduction of renal protein excretion, reduction of morbidity and mortality under experimental conditions. These experimental conditions consist of healthy animals on the one hand, or else of animals suffering from hypertension, heart and/or kidney failure (e.g. transgenic renin rats), L-NAME-treated animals (e.g. transgenic renin rats+L-NAME treatment).

Preference is given to combinations comprising at least one sGC activator and at least one MR antagonist.

Preference is also given to combinations comprising at least one sGC activator and at least one steroidal MR antagonist.

Preference is also given to combinations comprising at least one sGC activator and at least one non-steroidal MR antagonist.

Preference is also given to combinations comprising at least one sGC activator and at least one non-steroidal MR antagonist having a dihydropyridine skeleton.

Preference is also given to combinations comprising at least one sGC activator and at least one non-steroidal MR antagonist having an indole or indazole skeleton.

Preference is also given to combinations comprising at least one sGC activator and at least one non-steroidal MR antagonist having an oxazolidinedione skeleton.

Preference is also given to combinations comprising at least one sGC activator and at least one steroidal MR antagonist selected from the group consisting of spironolactone (7α-acetylthio-3-oxo-17α-pregn-4-ene-21,17β-carbolacto-7α-acetylthio-3-oxo-17α-pregn-4-ene-21,17β-carbolactone) of the formula (I)

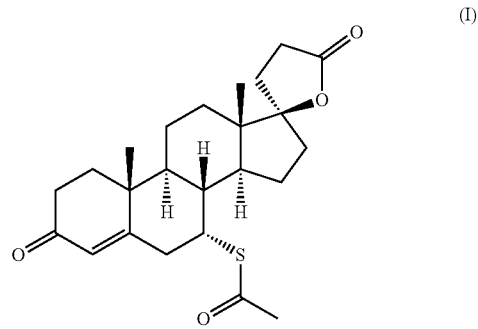

eplerenone (epoxymexerenone) of the formula (II)

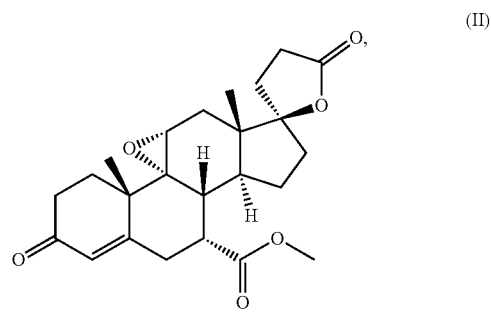

kanrenone (10,13-dimethylspiro[2,8,9,11,12,14,15,16-octahydro-1H-cyclopenta[a]phenanthrene-17,5'-oxolane]-2',3-dione) of the formula (III)

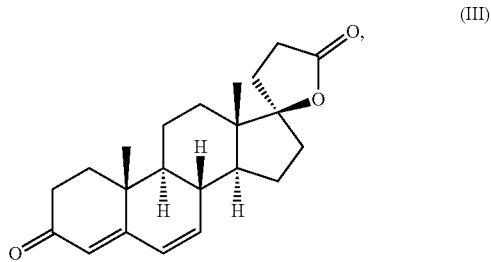

and its potassium salt (potassium kanrenoate).

Preference is also given to combinations comprising at least one sGC activator and at least one non-steroidal MR antagonist selected from the group consisting of finerenone ((S)-4-(4-cyano-2-methoxyphenyl)-5-ethoxy-2,8-dimethyl-1,4-dihydro-1,6-naphthyridine-3-carboxamide) of the formula (IV)

(R)-6-(1-(4-cyano-3-methylphenyl)-5-cyclopentyl-4,5-dihydro-1H-pyrazol-3-yl)-2-methoxynicotinic acid of the formula (VIII)

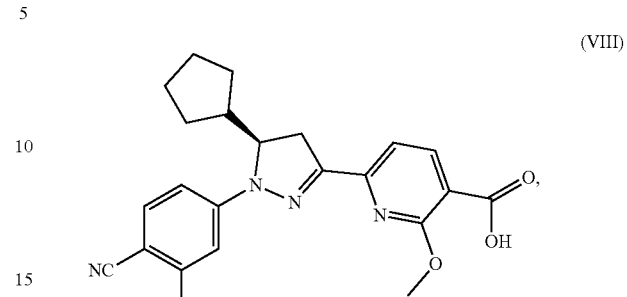

(VIII)

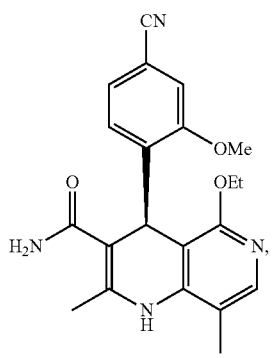

(IV)

esaxerenone (1-(2-hydroxyethyl)-4-methyl-N-(4-(methylsulfonyl)phenyl)-5-(2-(trifluoromethyl) phenyl)-1H-pyrrole-3-carboxamide) of the formula (V)

(S)—N-{3-[1-cyclopropyl-1-(2,4-difluorophenyl)ethyl]-1H-indol-7-yl}methanesulfonamide of the formula (IX)

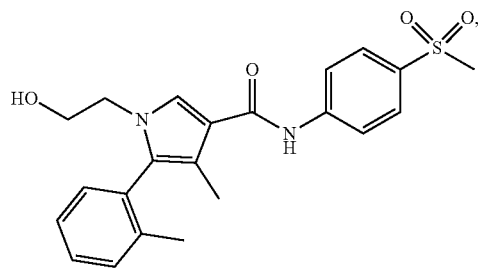

(V)

aparerenone (N-(4-(4-fluorophenyl)-2,2-dimethyl-3-oxo-3,4-dihydro-2H-benzo[b][1,4]oxazin-7-yl)methanesulfonamide) of the formula (VI)

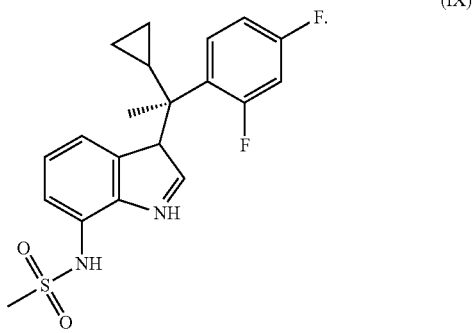

(IX)

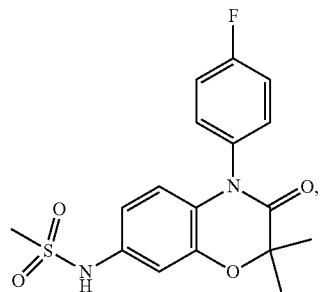

(VI)

Preference is also given to combinations comprising at least one sGC activator and finerenone, (S)-4-(4-cyano-2-methoxyphenyl)-5-ethoxy-2,8-dimethyl-1,4-dihydro-1,6-naphthyridine-3-carboxamide of the formula (IV)

(3S,3aR)-2-(3-chloro-4-cyanophenyl)-3-cyclopentyl-3,3a,4,5-tetrahydro-2H-benzo[g]indazole-7-carboxylic acid) of the formula (XIV)

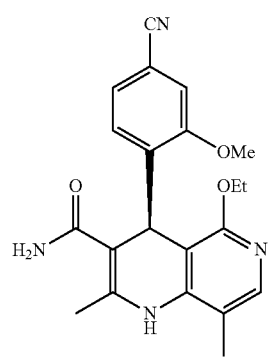

(IV)

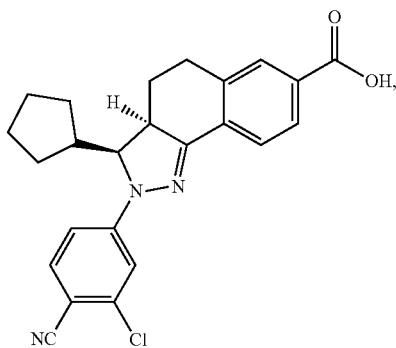

(XIV)

Preference is also given to combinations comprising at least one sGC activator comprising at least one carboxylic acid function and finerenone, (S)-4-(4-cyano-2-methoxyphenyl)-5-ethoxy-2,8-dimethyl-1,4-dihydro-1,6-naphthyridine-3-carboxamide of the formula (IV)

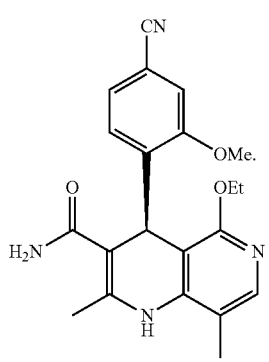

Preference is also given to combinations comprising at least one sGC activator selected from the group consisting of (3S)-3-(4-chloro-3-{[(2S,3R)-2-(4-chlorophenyl)-4,4,4-trifluoro-3-methylbutanoyl]amino}phenyl)-3-cyclopropyl-propanoic acid of the formula (X)

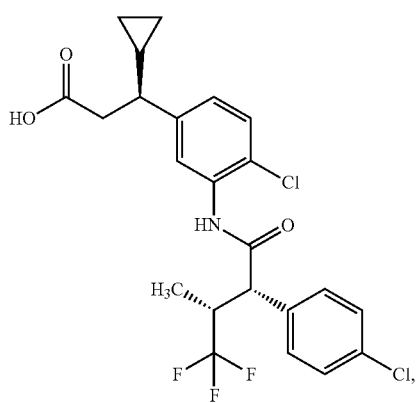

4-({(4-carboxybutyl)[2-(2-{[4-(2-phenylethyl)benzyl]oxy}phenyl)ethyl]amino}methyl)carboxylic acid of the formula (XI)

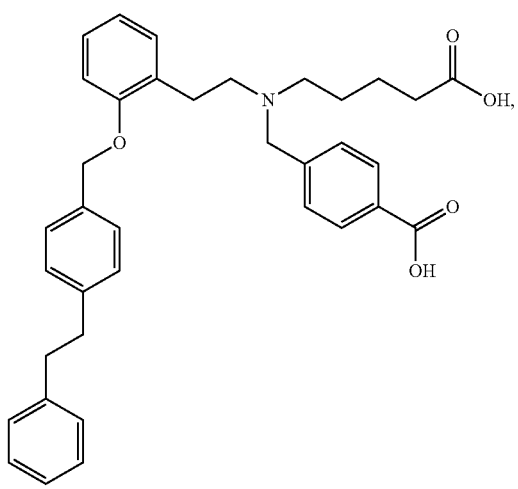

5-{(4-carboxybutyl)[2-(2-{[3-chloro-4'-(trifluoromethyl)biphenyl-4-yl]methoxy}phenyl)ethyl]amino}-5,6,7,8-tetrahydroquinoline-2-carboxylic acid of the formula (XII)

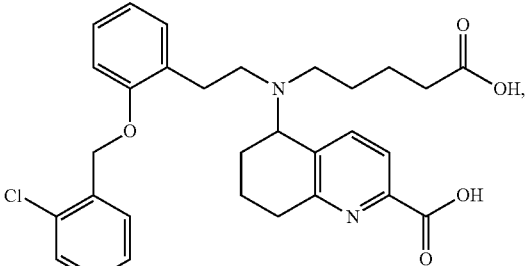

5-{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid of the formula (XIII)

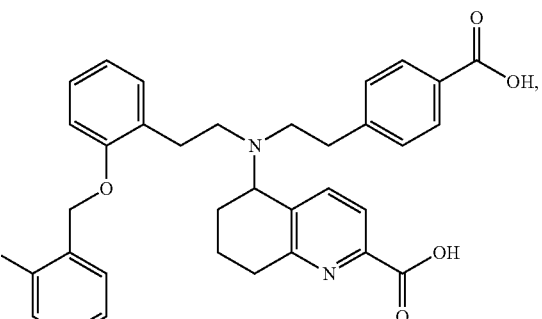

and finerenone, (S)-4-(4-cyano-2-methoxyphenyl)-5-ethoxy-2,8-dimethyl-1,4-dihydro-1,6-naphthyridine-3-carboxamide of the formula (IV)

(IV)

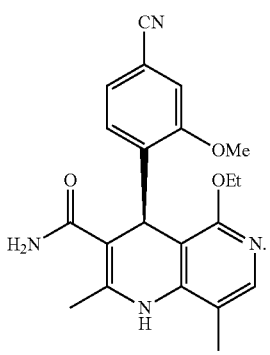

Preference is also given to combinations comprising at least one sGC activator, comprising at least one carboxylic acid function and at least one MR antagonist.

Preference is also given to combinations comprising at least one sGC activator, comprising a carboxylic acid function and at least one MR antagonist.

Preference is also given to combinations comprising at least one sGC activator selected from the group consisting of (3S)-3-(4-chloro-3-{[(2S,3R)-2-(4-chlorophenyl)-4,4,4-trifluoro-3-methylbutanoyl]amino}phenyl)-3-cyclopropylpropanoic acid of the formula (X)

(X)

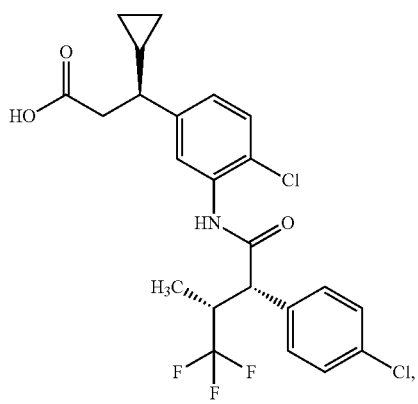

4-({(4-carboxybutyl)[2-(2-{[4-(2-phenylethyl)benzyl]oxy}phenyl)ethyl]amino}methyl)carboxylic acid of the formula (XI)

(XI)

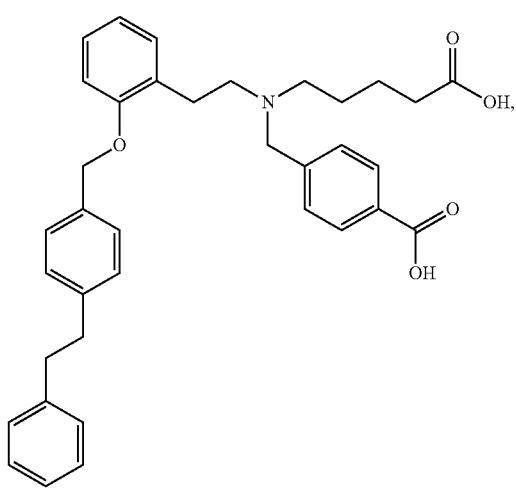

5-{(4-carboxybutyl)[2-(2-{[3-chloro-4'-(trifluoromethyl)biphenyl-4-yl]methoxy}phenyl)ethyl]amino}-5,6,7,8-tetrahydroquinoline-2-carboxylic acid of the formula (XII)

(XII)

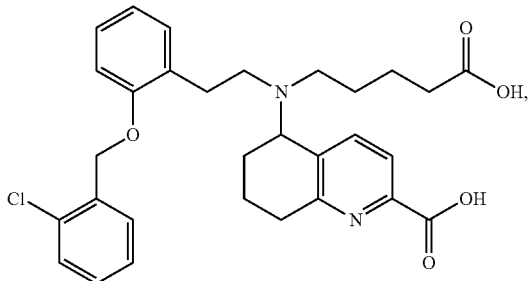

5-{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid of the formula (XIII)

(XIII)

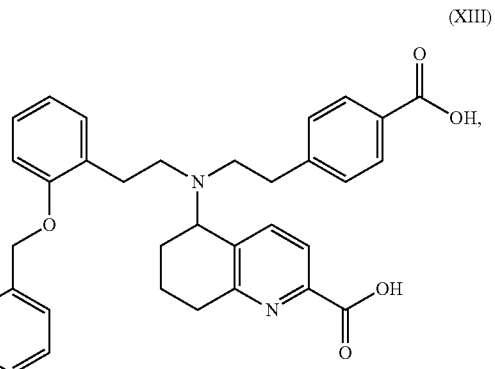

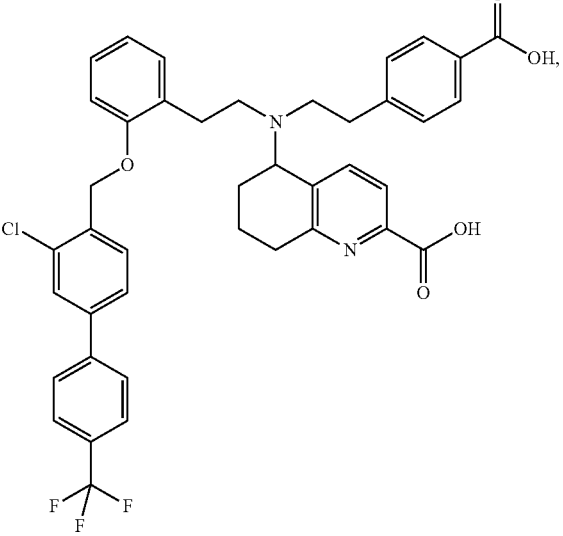

and an MR antagonist.

Preference is also given to combinations comprising the sGC activator (3S)-3-(4-chloro-3-{[(2S,3R)-2-(4-chlorophenyl)-4,4,4-trifluoro-3-methylbutanoyl]amino}phenyl)-3-cyclopropylpropanoic acid of the formula (X)

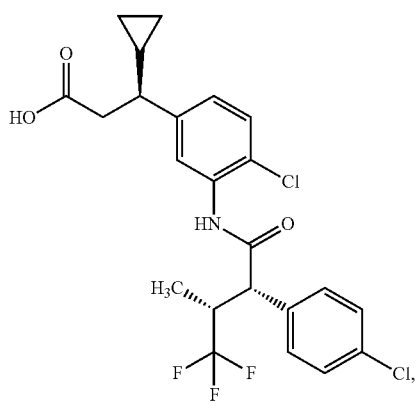

and at least one MR antagonist.

Particular preference is given to combinations comprising the sGC activator (3S)-3-(4-chloro-3-{[(2S,3R)-2-(4-chlorophenyl)-4,4,4-trifluoro-3-methylbutanoyl]amino}phenyl)-3-cyclopropylpropanoic acid of the formula (X)

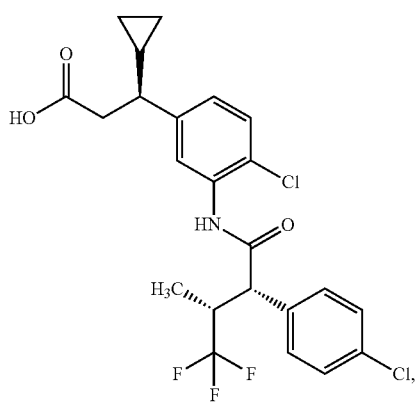

and at least one steroidal MR antagonist.

Particular preference is given to combinations comprising the sGC activator (3S)-3-(4-chloro-3-{[(2S,3R)-2-(4-chlorophenyl)-4,4,4-trifluoro-3-methylbutanoyl]amino}phenyl)-3-cyclopropylpropanoic acid of the formula (X)

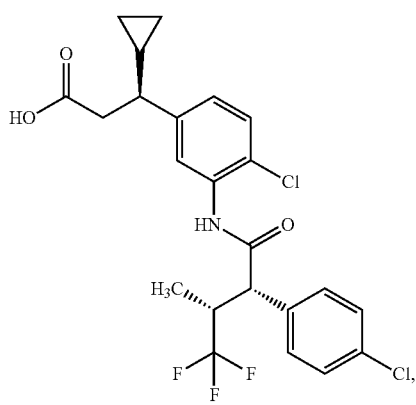

and at least one non-steroidal MR antagonist.

Particular preference is given to combinations comprising the sGC activator (3S)-3-(4-chloro-3-{[(2S,3R)-2-(4-chlorophenyl)-4,4,4-trifluoro-3-methylbutanoyl]amino}phenyl)-3-cyclopropylpropanoic acid of the formula (X)

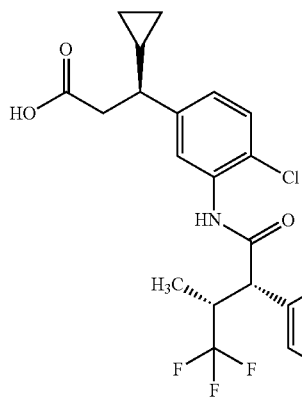

and at least one non-steroidal MR antagonist based on a dihydropyridine skeleton.

Particular preference is given to combinations comprising the sGC activator (3S)-3-(4-chloro-3-{[(2S,3R)-2-(4-chlorophenyl)-4,4,4-trifluoro-3-methylbutanoyl]amino}phenyl)-3-cyclopropylpropanoic acid of the formula (X)

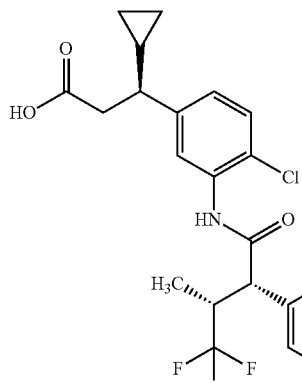

and at least one non-steroidal MR antagonist based on an indole or indazole skeleton.

Particular preference is given to combinations comprising the sGC activator (3S)-3-(4-chloro-3-{[(2S,3R)-2-(4-chlorophenyl)-4,4,4-trifluoro-3-methylbutanoyl]amino}phenyl)-3-cyclopropylpropanoic acid of the formula (X)

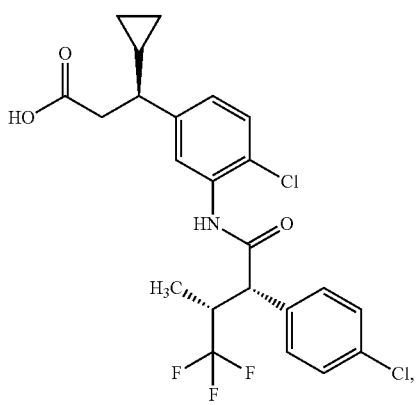

(X)

and at least one non-steroidal MR antagonist based on an oxazolidinedione skeleton.

Particular preference is given to combinations comprising the sGC activator (3S)-3-(4-chloro-3-{[(2S,3R)-2-(4-chlorophenyl)-4,4,4-trifluoro-3-methylbutanoyl]amino}phenyl)-3-cyclopropylpropanoic acid of the formula (X)

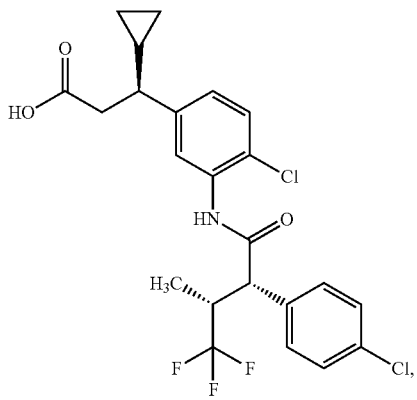

(X)

and at least one steroidal MR antagonist selected from the group consisting of spironolactone (7α-acetylthio-3-oxo-17α-pregn-4-ene-21,17β-carbolacto-7α-acetylthio-3-oxo-17α-pregn-4-ene-21,17β-carbolactone) of the formula (I)

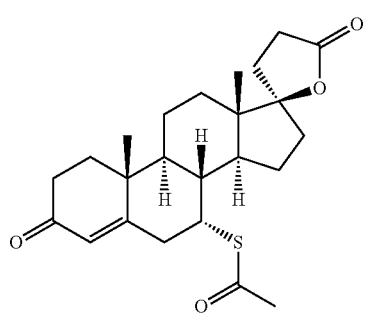

(I)

eplerenone (epoxymexerenone) of the formula (II)

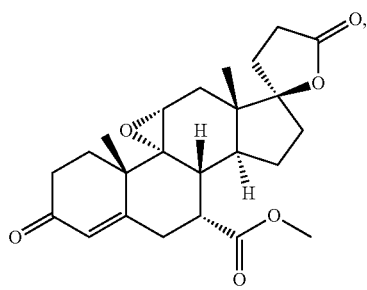

(II)

kanrenone (10,13-dimethylspiro[2,8,9,11,12,14,15,16-octahydro-1H-cyclopenta[a]phenanthrene-17,5'-oxolane]-2',3-dione) of the formula (III)

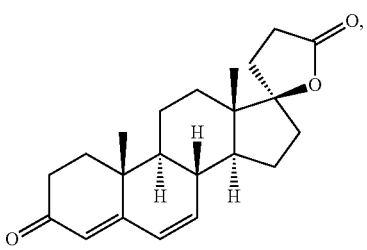

(III)

and its potassium salt.

Particular preference is given to combinations comprising the sGC activator (3S)-3-(4-chloro-3-{[(2S,3R)-2-(4-chlorophenyl)-4,4,4-trifluoro-3-methylbutanoyl]amino}phenyl)-3-cyclopropylpropanoic acid of the formula (X)

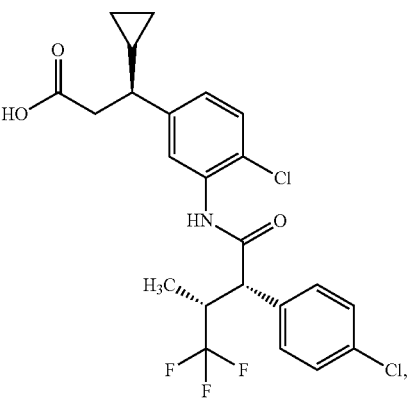

(X)

and at least one non-steroidal MR antagonist selected from the group consisting of finerenone ((S)-4-(4-cyano-2-methoxyphenyl)-5-ethoxy-2,8-dimethyl-1,4-dihydro-1,6-naphthyridine-3-carboxamide) of the formula (IV)

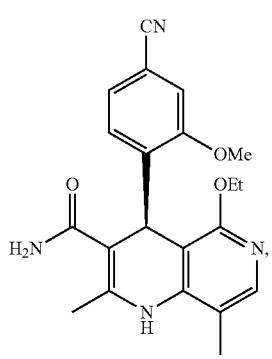

esaxerenone (1-(2-hydroxyethyl)-4-methyl-N-(4-(methylsulfonyl)phenyl)-5-(2-(trifluoromethyl) phenyl)-1H-pyrrole-3-carboxamide) of the formula (V)

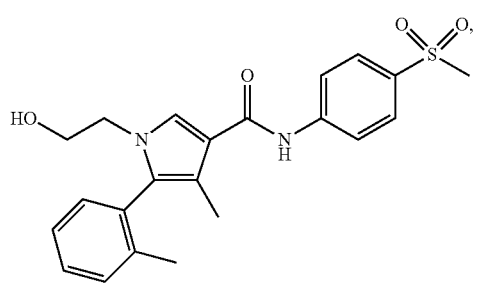

apararenone (N-(4-(4-fluorophenyl)-2,2-dimethyl-3-oxo-3,4-dihydro-2H-benzo[b][1,4]oxazin-7-yl)methanesulfonamide) of the formula (VI)

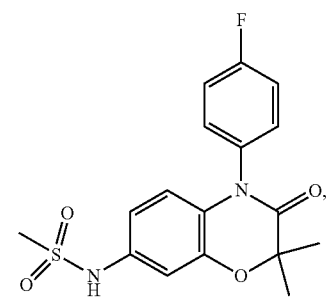

(3S,3aR)-2-(3-chloro-4-cyanophenyl)-3-cyclopentyl-3,3a,4,5-tetrahydro-2H-benzo[g]indazole-7-carboxylic acid) of the formula (XIV)

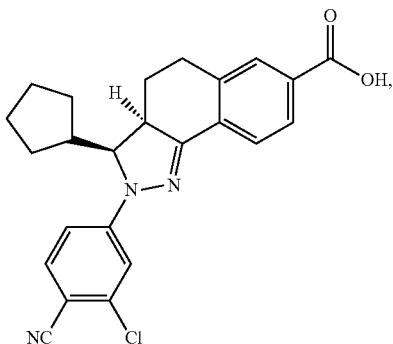

(R)-6-(1-(4-cyano-3-methylphenyl)-5-cyclopentyl-4,5-dihydro-1H-pyrazol-3-yl)-2-methoxynicotinic acid of the formula (VIII)

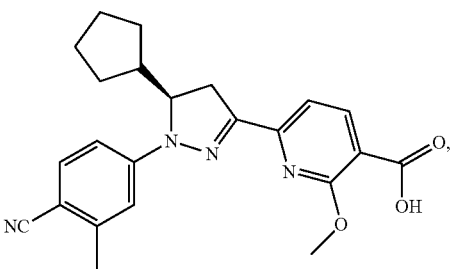

(S)—N-{3-[1-cyclopropyl-1-(2,4-difluorophenyl)ethyl]-1H-indol-7-yl}methanesulfonamide of the formula (IX)

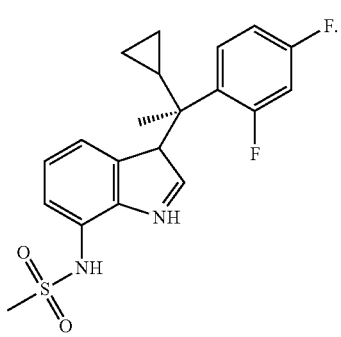

Very particular preference is given to the combination comprising the sGC activator (3S)-3-(4-chloro-3-{[(2S,3R)-2-(4-chlorophenyl)-4,4,4-trifluoro-3-methylbutanoyl]amino}phenyl)-3-cyclopropylpropanoic acid of the formula (X)

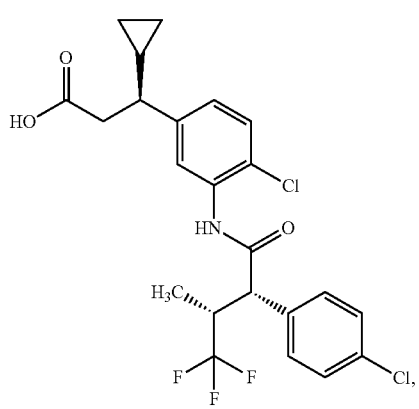

and (S)-4-(4-cyano-2-methoxyphenyl)-5-ethoxy-2,8-dimethyl-1,4-dihydro-1,6-naphthyridine-3-carboxamide of the formula (IV)

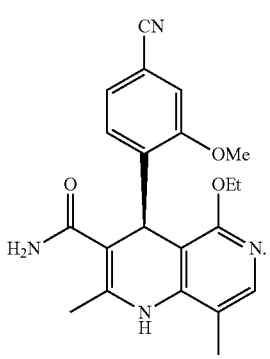

(IV)

Simultaneous blockade of binding of aldosterone to MR and of activation of soluble guanylate cyclase by sGC activators by the combination according to the invention results in superadditive effects with regard to end organ protection, reduction of renal protein excretion and reduction of morbidity and mortality.

The invention further provides the use of MR antagonists in combination with sGC activators for the treatment of cardiac and cardiovascular disorders such as heart failure with preserved ejection fraction or heart failure with reduced ejection fraction, treatment and/or prophylaxis of atrial fibrillation, stroke or atherosclerosis, for the treatment of renal and cardiorenal disorders such as chronic kidney failure or diabetic nephropathy, of lung disorders and cardiopulmonary disorders such as pulmonary disease hypertension, disorders of the central nervous system, for the treatment and/or prophylaxis of fibrotic disorders and other disease manifestations (e.g. end organ damage affecting brain, kidney, heart or lung).

Part of the subject matter of the present invention is a pharmaceutical formulation comprising a combination of an MR antagonist and an sGC activator, and also salts, solvates and solvates of the salts of the components to be combined.

The components to be combined may be present as salts. Preferred salts in the context of the present invention are physiologically acceptable salts of the compounds to be combined. Also included are salts which are not themselves suitable for pharmaceutical applications but can be used, for example, for isolation or purification of the compounds to be combined.

The combination according to the invention is suitable for the prophylaxis and/or treatment of various disorders and disease-related states, in particular for the treatment and/or prophylaxis of cardiac and cardiovascular disorders such as heart failure with preserved ejection fraction or heart failure with reduced ejection fraction, treatment and/or prophylaxis of atrial fibrillation, stroke or atherosclerosis, renal and cardiorenal disorders such as chronic kidney failure or diabetic nephropathy, of lung disorders and cardiopulmonary disorders such as pulmonary disease hypertension, disorders of the central nervous system, for the treatment and/or prophylaxis of fibrotic disorders and other disease manifestations (e.g. end organ damage affecting brain, kidney or heart).

Furthermore, the combinations according to the invention are suitable for the prophylaxis and/or treatment of various disorders and disease-related states, in particular for the treatment and/or prophylaxis of a disease selected from the group consisting of hypertension, heart failure (acute and chronic), decompensated heart failure, left ventricular dysfunction, hypertrophic cardiomyopathy, diabetic cardiomyopathy, supraventricular and ventricular arrythmias, atrial fibrillation, atrial flutter, detrimental vascular remodelling, myocardial infarction and sequelae thereof, atherosclerosis, angina (unstable or stable), renal failure (diabetic and non-diabetic), heart failure, angina pectoris, diabetes, secondary hyperaldosteronism, primary and secondary pulmonary hypertension, glomerulonephritis, scleroderma and systemic sclerosis, glomerular sclerosis, proteinuria as sequela of a primary kidney disease, renal vascular hypertension, diabetic and non-diabetic retinopathy, migraine, peripheral vascular disease, Raynaud disease, luminal hyperplasia, cognitive dysfunction, glaucoma and stroke.

The present invention further provides for the use of the combinations of the invention for production of a medicament for the treatment and/or prevention of disorders, especially of the aforementioned disorders.

The present invention further provides a method for the treatment and/or prevention of disorders, in particular the disorders mentioned above.

The combinations according to the invention can be used alone or, if required, in combination with other active compounds. The present invention further provides medicaments comprising at least one of the combinations according to the invention and one or more further active compounds, especially for the treatment and/or prevention of the aforementioned disorders. Preferred examples of active compounds suitable for combinations include:

active compounds which lower blood pressure, for example and with preference from the group of calcium antagonists, angiotensin receptor blockers (ARBs), ACE inhibitors, endothelin antagonists, renin inhibitors, alpha-receptor blockers, beta-receptor blockers and Rho kinase inhibitors;

diuretics, especially loop diuretics, and thiazides and thiazide-like diuretics;

antidiabetics, for example and with preference insulin and derivatives, sulfonylureas, biguanides, thiazolidinediones, acarbose, DPP4 inhibitors, GLP-1 analogues or SGLT inhibitors (gliflozin);

antithrombotic agents, by way of example and with preference from the group of the platelet aggregation inhibitors, the anticoagulants or the profibrinolytic substances;

active ingredients which alter lipid metabolism, for example and with preference from the group of thyroid receptor agonists, cholesterol synthesis inhibitors, preferred examples being HMG-CoA reductase inhibitors or squalene synthesis inhibitors, of ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbents, bile acid reabsorption inhibitors and lipoprotein(a) antagonists;

organic nitrates and NO donors, for example sodium nitroprusside, nitroglycerin, isosorbide mononitrate, isosorbide dinitrate, molsidomine or SIN-1, and inhaled NO;

compounds having a positive inotropic effect, for example cardiac glycosides (digoxin), beta-adrenergic and dopaminergic agonists such as isoproterenol, adrenaline, noradrenaline, dopamine and dobutamine;

compounds which inhibit the degradation of cyclic guanosine monophosphate (cGMP) and/or cyclic adenosine monophosphate (cAMP), for example inhibitors of phosphodiesterases (PDE) 1, 2, 3, 4 and/or 5, especially PDE 5 inhibitors such as sildenafil, vardenafil and tadalafil, and PDE 3 inhibitors such as amrinone and milrinone;

natriuretic peptides, for example atrial natriuretic peptide (ANP, anaritide), B-type natriuretic peptide or brain natriuretic peptide (BNP, nesiritide), C-type natriuretic peptide (CNP) and urodilatin;

inhibitors of endopeptidases (NEP inhibitors) such as sacubitril, omapatrilate or AVE-7688, or in dual combination ('ARNIs') with angiotensin receptor blockers (e.g. valsartan), e.g. LCZ696;

calcium sensitizers, for example and with preference levosimendan;

If channel blockers, for example and with preference ivabradine;

myosin activators, for example and with preference omecamtiv mecarbil;

inhibitors of human neutrophil elastase (HNE), for example sivelestat or DX-890 (Reltran);

compounds which inhibit the signal transduction cascade, for example tyrosine kinase inhibitors, especially sorafenib, imatinib, gefitinib and erlotinib; and/or compounds which influence the energy metabolism of the heart, by way of example and with preference etomoxir, dichloroacetate, ranolazine or trimetazidine;

In a preferred embodiment of the invention, the combination of the invention is administered in combination with a diuretic, by way of example and with preference furosemide, bumetanide, torsemide, bendroflumethiazide, chlorothiazide, hydrochlorothiazide, hydroflumethiazide, methyclothiazide, polythiazide, trichlormethiazide, chlorthalidone, indapamide, metolazone, quinethazone, acetazolamide, dichlorphenamide, methazolamide, glycerol, isosorbide, mannitol, amiloride or triamterene.

Agents which lower blood pressure are preferably understood to mean compounds from the group of calcium antagonists, angiotensin receptor blockers, ACE inhibitors, endothelin antagonists, renin inhibitors, alpha-receptor blockers, beta-receptor blockers, Rho kinase inhibitors, and the diuretics.

In a preferred embodiment of the invention, the combination preparation according to the invention is administered in combination with an antidiabetic such as, by way of example and with preference, insulin and derivatives, sulfonylureas such as tolbutamide, carbutamide, acetohexamide, chlorpropamide, glipizide, gliclazide, glibenclamide, glyburide, glibornuride, gliquidone, glisoxepide, glyclopyramide, glimepiride, JB253 and JB558, meglitinides such as repaglinide and nateglinide, biguanides such as metformin and buformin, thiazolidinediones such as rosiglitazone and pioglitazone, alpha-glucosidase inhibitors such as miglitol, acarbose and voglibose, DPP4 inhibitors such as vildagliptin, sitagliptin, saxagliptin, linagliptin, alogliptin, septagliptin and tenegliptin, GLP-1 analogues such as exenatide (also exendin-4), liraglutide, lixisenatide and taspoglutide, or SGLT inhibitors (gliflozins) such as canagliflozin, dapagliflozin and empagliflozin.

In a preferred embodiment of the invention, the combination according to the invention is administered in combination with a calcium antagonist, by way of example and with preference nifedipine, amlodipine, verapamil or diltiazem.

In a preferred embodiment of the invention, the compounds of the invention are administered in combination with an angiotensin AII antagonist, by way of example and with preference losartan, candesartan, valsartan, olmesartan, telmisartan or embursatan.

In a preferred embodiment of the invention, the combination according to the invention is administered in combination with an ACE inhibitor, by way of example and with preference enalapril, captopril, lisinopril, ramipril, delapril, fosinopril, quinopril, perindopril or trandopril.

In a preferred embodiment of the invention, the combination according to the invention is administered in combination with an endothelin antagonist, by way of example and with preference bosentan, darusentan, ambrisentan or sitaxsentan.

In a preferred embodiment of the invention, the combination according to the invention is administered in combination with a renin inhibitor, by way of example and with preference aliskiren, SPP-600, SPP-635, SPP-676, SPP-800 or SPP-1148.

In a preferred embodiment of the invention, the combination according to the invention is administered in combination with an alpha-1 receptor blocker, by way of example and with preference prazosin.

In a preferred embodiment of the invention, the combination according to the invention is administered in combination with a beta receptor blocker, by way of example and with preference propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the combination according to the invention is administered in combination with a Rho kinase inhibitor, by way of example and with preference fasudil, Y-27632, SLx-2119, BF-66851, BF-66852, BF-66853, KI-23095 or BA-1049.

In a preferred embodiment of the invention, the combination according to the invention is administered in combination with prostanoids and prostacyclin receptor agonists, by way of example and with preference iloprost, beraprost, cicaprost, epoprostenol or treprostinil.

Antithrombotic agents (antithrombotics) are preferably understood to mean compositions from the group of platelet aggregation inhibitors, of anticoagulants or of profibrinolytic substances.

In a preferred embodiment of the invention, the combination according to the invention is administered in combination with a platelet aggregation inhibitor, by way of example and with preference aspirin, clopidogrel, ticlopidine or dipyridamole.

In a preferred embodiment of the invention, the combination according to the invention is administered in combination with a thrombin inhibitor, by way of example and with preference ximelagatran, melagatran, bivalirudin or clexane.

In a preferred embodiment of the invention, the combination according to the invention is administered in combination with a GPIIb/IIIa antagonist, by way of example and with preference tirofiban or abciximab.

In a preferred embodiment of the invention, the combination according to the invention is administered in combination with a factor Xa inhibitor, by way of example and with preference rivaroxaban (BAY 59-7939), DU-176b, apixaban, otamixaban, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the combination according to the invention is administered in combination with heparin or with a low molecular weight (LMW) heparin derivative.

In a preferred embodiment of the invention, the combination according to the invention is administered in combination with a vitamin K antagonist, by way of example and with preference coumarin.

Lipid metabolism modifiers are preferably understood to mean compounds from the group of the CETP inhibitors, thyroid receptor agonists, cholesterol synthesis inhibitors such as HMG-CoA reductase inhibitors or squalene synthesis inhibitors, the ACAT inhibitors, MTP inhibitors, PPAR-alpha, PPAR-gamma and/or PPAR-delta agonists, cholesterol absorption inhibitors, polymeric bile acid adsorbers, bile acid reabsorption inhibitors, lipase inhibitors and the lipoprotein(a) antagonists.

In a preferred embodiment of the invention, the combination according to the invention is administered with a CETP inhibitor, by way of example and with preference torcetrapib (CP-529 414), JJT-705, BAY 60-5521, BAY 78-7499 or CETP vaccine (Avant).

In a preferred embodiment of the invention, the combination according to the invention is administered in combination with a thyroid receptor agonist, by way of example and with preference D-thyroxine, 3,5,3'-triiodothyronine (T3), CGS 23425 or axitirome (CGS 26214).

In a preferred embodiment of the invention, the combination according to the invention is administered in combination with an HMG-CoA reductase inhibitor from the class of statins, by way of example and with preference lovastatin, simvastatin, pravastatin, fluvastatin, atorvastatin, rosuvastatin, cerivastatin or pitavastatin.

In a preferred embodiment of the invention, the combination according to the invention is administered in combination with a squalene synthesis inhibitor, by way of example and with preference BMS-188494 or TAK-475.

In a preferred embodiment of the invention, the combination according to the invention is administered in combination with an ACAT inhibitor, by way of example and with preference avasimibe, melinamide, pactimibe, eflucimibe or SMP-797.

In a preferred embodiment of the invention, the combination according to the invention is administered in combination with an MTP inhibitor, by way of example and with preference implitapide, BMS-201038, R-103757 or JTT-130.

In a preferred embodiment of the invention, the combination according to the invention is administered in combination with a PPAR-gamma agonist, by way of example and with preference pioglitazone or rosiglitazone.

In a preferred embodiment of the invention, the combination according to the invention is administered with a PPAR-delta agonist, by way of example and with preference GW-501516 or BAY 68-5042.

In a preferred embodiment of the invention, the combination according to the invention is administered with a cholesterol absorption inhibitor, by way of example and with preference ezetimibe, tiqueside or pamaqueside.

In a preferred embodiment of the invention, the combination according to the invention is administered with a lipase inhibitor, by way of example and with preference orlistat.

In a preferred embodiment of the invention, the combination according to the invention is administered in combination with a polymeric bile acid adsorber, by way of example and with preference cholestyramine, colestipol, colesolvam, CholestaGel or colestimide.

In a preferred embodiment of the invention, the combination according to the invention is administered in combination with a bile acid reabsorption inhibitor, by way of example and with preference ASBT (=IBAT) inhibitors, for example AZD-7806, S-8921, AK-105, BARI-1741, SC-435 or SC-635.

In a preferred embodiment of the invention, the combination according to the invention is administered in combination with a lipoprotein(a) antagonist, by way of example and with preference gemcabene calcium (CI-1027) or nicotinic acid.

In the preferred embodiment of the invention, the combination according to the invention is administered in combination with compounds having antifibrotic action, such as, by way of example and with preference, sorafenib, regorafenib, imatinib, dasatinib, nilotinib, nintedanib, bortezomib or pirfenidone.

In the preferred embodiment of the invention, the combination according to the invention is administered in combination with compounds having antiinflammatory action, such as, by way of example and with preference, cyclophosphamide, methotrexate, rapamycin, azathioproin, tocilizumab, infliximab, rituximab, adalimumab, belimumab, abatacept, SAR100842 or thalidomide derivatives.

The combinations according to the invention can act systemically and/or locally. For this purpose, they can be administered in a suitable manner, for example by the oral, parenteral, pulmonal, nasal, sublingual, lingual, buccal, rectal, dermal, transdermal, conjunctival or otic route, or as an implant or stent.

The combinations according to the invention can be administered in administration forms suitable for these administration routes.

Suitable administration forms for oral administration are those which work according to the prior art and release the combinations of the invention rapidly and/or in a modified manner and which contain the compounds of the invention in crystalline and/or amorphized and/or dissolved form, for example tablets (uncoated or coated tablets, for example with enteric coatings or coatings which dissolve in a delayed manner or insoluble coatings which control the release of the combinations of the invention), tablets or films/wafers which disintegrate rapidly in the oral cavity, films/lyophilizates, capsules (for example hard or soft gelatin capsules), sugar-coated tablets, granules, pellets, powders, emulsions, suspensions, aerosols or solutions.

Preferred administration forms that may be mentioned are tablet forms (uncoated or coated tablets, for example with enteric coatings or coatings which dissolve in a delayed manner or insoluble coatings which control the release of the combinations according to the invention), tablets which disintegrate rapidly in the mouth or films/wafers.

Parenteral administration can be accomplished with avoidance of a resorption step (for example by an intravenous, intraarterial, intracardiac, intraspinal or intralumbar route) or with inclusion of a resorption (for example by an intramuscular, subcutaneous, intracutaneous, percutaneous or intraperitoneal route). Administration forms suitable for parenteral administration include inter alia preparations for injection and infusion in the form of solutions, suspensions, emulsions, lyophilizates or sterile powders.

For the other administration routes, suitable examples are inhalation medicaments (including powder inhalers, nebulizers), nasal drops, solutions or sprays, tablets for lingual, sublingual or buccal administration, films/wafers or capsules, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, dusting powders, implants or stents.

Preference is given to oral or parenteral administration, oral administration being more preferred. Particular preference is given to oral administration by means of tablet form.

The combinations according to the invention can be converted to the administration forms mentioned. This can be accomplished in a manner known per se by mixing with inert, non-toxic, pharmaceutically suitable excipients. These excipients include inter alia carriers (for example microcrystalline cellulose, lactose, mannitol), solvents (e.g. liquid polyethylene glycols), emulsifiers and dispersing or wetting agents (for example sodium dodecylsulfate, polyoxysorbitan oleate), binders (for example polyvinylpyrrolidone), synthetic and natural polymers (for example albumin), stabilizers (e.g. antioxidants, for example ascorbic acid), colourants (e.g. inorganic pigments, for example iron oxides) and flavour and/or odour correctors.

In the combinations according to the invention, the components may be administered together or successively or separately in a combined unit dosage form or in two separate unit dosage forms. The unit dosage form may also be a fixed combination.

A therapeutically effective amount of each component of the combination according to the invention may be administered simultaneously or sequentially in any sequence.

In one embodiment, the components may be present in a so-called delayed-release formulation in which the release of the components according to the invention takes place at different times. By way of example, mention may be made of a tablet with delayed-dissolution coatings, each of which contains one or more components according to the invention.

If the components of the combination according to the invention are administered in separate unit dosage forms, the MR antagonists and sGC activators can each be provided, for example, as a capsule or tablet.

In the case of oral administration, the dosage of finerenone according to the compound of the formula (IV) is for example about 1 to 100 mg od, preferably about 2.5 to 50 mg od and very particularly preferably 10 to 40 mg od.

It may nevertheless be necessary in some cases to deviate from the stated amounts, and specifically as a function of body weight, route of administration, individual response to the active ingredient, nature of the preparation and time at which or interval over which administration takes place. Thus in some cases it may be sufficient to manage with less than the aforementioned minimum amount, while in other cases the upper limit mentioned must be exceeded. In the case of administration of greater amounts, it may be advisable to divide them into several individual doses over the day.

The invention also relates to the combination of separate pharmaceutical compositions in kit form. This is a kit comprising two separate units: a pharmaceutical composition of at least one MR antagonist and a pharmaceutical composition of at least one sGC activator.

The invention also relates to a preferred kit form comprising two units: a pharmaceutical composition comprising at least one MR antagonist and a pharmaceutical composition comprising at least one sGC activator.

The kit is particularly advantageous if the separate components have to be administered in different dose forms or are administered in different dose intervals.

Working Examples of Pharmaceutical Compositions

The compounds of the invention can be converted to pharmaceutical preparations as follows:

Tablet:

Pharmaceutical Formulation of finerenone (4S)-4-(4-cyano-2-methoxyphenyl)-5-ethoxy-2,8-dimethyl-1,4-dihydro-1,6-naphthyridine-3-carboxamide of the formula (IV)

A granular solution of the compound of the formula (IV) in crystalline form in micronized form, hypromellose 5 cP and sodium lauryl sulfate was prepared in purified water.

Microcrystalline cellulose, lactose monohydrate and croscarmellose sodium were mixed (premix) in a container or a fluidized bed granulator.

The premix and the granular solution were granulated in the fluid-bed granulator.

The lubricant magnesium stearate was added after which the granulate was dried and sieved. A ready to press mixture was thus prepared.

The ready to press mixture was compressed to give tablets using a rotary tablet press.

A homogeneous coating suspension was prepared from hypromellose, talc, titanium dioxide, yellow iron oxide, red iron oxide and purified water. The coating suspension was sprayed onto the tablets in a suitable coating device.

| Composition | Ph IIb [mg] | Ph IIb [mg] | Ph IIb [mg] | Ph IIb [mg] | Ph IIb [mg] | Ph IIb [mg] | Ph IIb [mg] |
|---|---|---|---|---|---|---|---|
| Compound | | | | | | | |
| of the formula (IV) micronized | 1.25 | 2.50 | 5.00 | 7.50 | 10.00 | 15.00 | 20.00 |
| Excipients | | | | | | | |
| Microcrystalline cellulose | 73.80 | 72.50 | 69.90 | 67.30 | 64.70 | 62.00 | 59.30 |
| Croscarmellose sodium | 4.50 | 4.50 | 4.50 | 4.50 | 4.50 | 4.50 | 4.50 |
| Hypromellose 5 cP | 4.50 | 4.50 | 4.50 | 4.50 | 4.50 | 4.50 | 4.50 |
| Lactose monohydrate | 45.00 | 45.00 | 45.00 | 45.00 | 45.00 | 42.50 | 40.00 |
| Magnesium stearate | 0.90 | 0.90 | 0.90 | 0.90 | 0.90 | 0.90 | 0.90 |
| Sodium lauryl sulfate | 0.05 | 0.10 | 0.20 | 0.30 | 0.40 | 0.60 | 0.80 |
| Weight (uncoated tablets) | 130.00 | 130.00 | 130.00 | 130.00 | 130.00 | 130.00 | 130.00 |

-continued

| Composition | Ph IIb [mg] | Ph IIb [mg] | Ph IIb [mg] | Ph IIb [mg] | Ph IIb [mg] | Ph IIb [mg] | Ph IIb [mg] |
|---|---|---|---|---|---|---|---|
| Film-coating | | | | | | | |
| Hypromellose 5 cP | 3.0336 | 3.0336 | 3.0336 | 3.0336 | 3.0336 | 3.0336 | 3.0336 |
| Titanium dioxide | 2.3196 | 2.3196 | 2.3196 | 2.3196 | 2.3196 | 2.3196 | 2.3196 |
| Talc | 0.6072 | 0.6072 | 0.6072 | 0.6072 | 0.6072 | 0.6072 | 0.6072 |
| Yellow iron oxide | 0.0324 | 0.0324 | 0.0324 | 0.0324 | 0.0324 | 0.0324 | 0.0324 |
| Red iron oxide | 0.0072 | 0.0072 | 0.0072 | 0.0072 | 0.0072 | 0.0072 | 0.0072 |
| Weight (film-coating) | 6.0000 | 6.0000 | 6.0000 | 6.0000 | 6.0000 | 6.0000 | 6.0000 |
| Weight (coated tablet) | 136.00 | 136.00 | 136.00 | 136.00 | 136.00 | 136.00 | 136.00 |

Assessment of Physiological Efficacy

The suitability of the combinations according to the invention for the treatment of cardiac and cardiovascular disorders and renal and cardiorenal disorders and other disorders described in the application can be demonstrated in the following assay systems:

1.) In Vivo Assay for Detecting Natriuretic Activity on Conscious Rats in Metabolic Cages Wistar rats (body weight 250-450 g) are kept with free access to feed (Altromin) and drinking water. From approx. 72 hours before the start of the test, the animals receive, instead of the normal feed, exclusively reduced-salt feed with a sodium chloride content of 0.02% (ssniff R/M-H, 10 mm with 0.02% Na, S0602-E081, ssniff Spezialdiäten GmbH, D-59494 Soest, Germany). During the test, the animals are housed singly in metabolic cages suitable for rats of this weight class (Tecniplast Deutschland GmbH, D-82383 Hohenpeissenberg, Deutschland) with free access to reduced-salt feed and drinking water for about 24 hours. At the start of the test, the substance to be tested is administered into the animals' stomachs by means of gavage in a volume of 0.5 ml/kg of body weight of a suitable solvent. Control animals receive only solvent. Controls and substance tests are carried out in parallel on the same day. Control groups and substance-dose groups each consist of 6 to 8 animals. During the test, the urine excreted by the animals is continuously collected in a receiver on the base of the cage. The urine volume per unit time is determined separately for each animal, and the concentration of the sodium and potassium ions excreted in the urine is measured by standard methods of flame photometry. The measurement intervals are typically the period up to 8 hours after the start of the test (day interval) and the period from 8 to 24 hours after the start of the test (night interval).

2.) DOCA/Salt Model

Administration of deoxycorticosterone acetate (DOCA) in combination with a high-salt diet and unilateral kidney removal in rats induces hypertension which is characterized by relatively low renin levels. A consequence of this endocrine hypertension (DOCA is a direct precursor of aldosterone) is, depending on the chosen DOCA concentration, cardiac hypertrophy and further end organ damage, for example to the kidney, which is characterized by proteinuria and glomerulosclerosis, inter alia. It is thus possible in this rat model to investigate test substances for the presence of an antihypertrophic and end organ-protecting effect.

Male Sprague-Dawley (SD) rats of about 8 weeks in age (body weight between 250 and 300 grams) undergo left uninephrectomy. For this purpose, the rats are anaesthetized with 1.5-2% isoflurane in a mixture of 66% $N_2O$ and 33% $O_2$, and the kidney is removed through a flank incision. "Sham-operated" animals from which no kidney is removed serve later as control animals.

Uninephrectomized SD rats receive 1% sodium chloride in the drinking water and a subcutaneous injection of DOCA (from SIGMA, dissolved in sesame oil; high dose: 100 mg/kg/wk s.c.; normal dose: 30 mg/kg/wk s.c.) injected between the shoulder blades once a week.

The substances which are to be studied for their protective effect in vivo are administered by gavage or via the feed (Ssniff, Germany). One day before the start of the test, the animals are randomized and assigned to groups with an identical number of animals, usually n=8-15. During the entire experiment, drinking water and feed are available ad libitum to the animals. The substances (combinations) are administered via the feed or once a day by gavage for 4-12 weeks. Animals treated in the same way but receiving either only the solvent or the feed without test substance serve as placebo group.

At the end of the experiment, haemodynamic parameters (blood pressure, heart rate, inotropism [dp/dt], relaxation time [tau], maximum left ventricular pressure, left ventricular end-diastolic pressure [LVEDP]) may be measured, and also the weights of heart, kidney and lung, protein elimination and gene expression of biomarkers (e.g. BNP, brain natriuretic peptide, plasma renin activity, angiotensin and aldosterone) by RIA, ELISA or RT/TaqMan PCR following RNA isolation from cardiac and renal tissue determined.

3.) L-NAME-Treated Transgenic Renin Rat (TGR(mRen2)27) The transgenic renin rat 'TGR(mRen2)27' is a hypertensive rat line developed by Mullins and Ganten which overexpresses the Ren-2 gene of the mouse. Additional administration of the nitrogen monoxide synthase inhibitor L-NAME induces endothelial dysfunction which increases morbidity and mortality in this model. Unless subjected to life-long antihypertensive therapy, homozygous animals die of secondary complications such as heart and kidney failure or stroke.

Male TGR(mRen2)27 renin rats aged 10 to 20 weeks are randomized to different pharmacological treatment groups and a placebo group. In addition, the nitrogen monoxide synthase inhibitor L-NAME is administered via the drinking water in a concentration of 30 to 100 mg/l. During the entire experiment, drinking water and feed are available ad libitum to the animals. The substances are administered via the feed or daily by gavage for 4-10 weeks. Animals treated in the same way but receiving either only the solvent or the feed without test substance serve as placebo group. During the experiment, the systolic blood pressure is determined at regular intervals using a tail cuff, and proteinuria and urine electrolyte composition are determined by collecting the urine in metabolic cages. At the end of the experiment, haemodynamic parameters (blood pressure, heart rate, inotropism [dp/dt], relaxation time [tau], maximum left ventricular pressure, left ventricular end-diastolic pressure [LVEDP]) are measured, and the weights of heart, kidney and lung are determined, protein elimination and biomarkers (e.g. ANP, RIA Kit RK 005-24, Phoenix Pharmaceuticals, Inc., USA, cGMP, RIA Kit RE29075, IBL International GmbH, Hamburg, Germany, renin, angiotensin I, RIA Kit CA-1533, DiaSorin S.p.A., Italy, and aldosterone, P2714, DiaSorin S.p.A., Italy) and gene expression of biomarkers by RT/TaqMan PCR following RNA isolation from cardiac and renal tissue are determined.

EXAMPLES

Cardiac and cardiovascular disorders as well as renal and cardiorenal disorders are characterized by high patient morbidity and also high mortality. This morbidity and mortality, together with various risk factors such as hypertension, can be reproduced very accurately in the above-described animal model of the L-NAME-treated renin transgenic rat. Therefore, this animal model, for example, was used to investigate MR antagonists such as, for example, finerenone according to the compound of the formula (IV) and sGC activators such as, for example, the compound of the formula (X), and combinations of both:

For example, the MR antagonist finerenone, corresponding to the compound of the formula (IV), and the sGC activator, corresponding to the compound of the formula (X), were tested on their own and in combinations in TGR(mRen2)27 renin rats aged 10 to 20 weeks. In addition, the nitrogen monoxide synthase inhibitor L-NAME was administered via the drinking water in a concentration of 30 to 100 mg/l. During the entire experiment, drinking water and feed were available ad libitum to the animals. The substances were administered daily by gavage for 4-10 weeks. Animals treated in the same way but receiving only the solvent for the test substance served as placebo group. In the test series, in addition to placebo (group A), the MR antagonist finerenone (10 mg/kg od) (group B) and the sGC activator corresponding to the compound of the formula (X) (1 mg/kg bid) (group C) on their own and a combination of finerenone (10 mg/kg od)+compound of the formula (X) (1 mg/kg bid) (group D) were administered. In this study, 15 animals were used per group (A, B, C, D) (Table 1):

TABLE 1

Group classification, treatment, dosage employed and administration protocol (od = once daily; bid = bidaily) and group size of the L-NAME-treated renin transgenic rats.

| Group name | Treatment | Dose | Group size [n] |
|---|---|---|---|
| Group A | placebo | | 15 |
| Group B | finerenone (compound of the formula (IV)) | 10 mg/kg od | 15 |
| Group C | Compound of the formula (X) | 1 mg/kg bid | 15 |
| Group D | finerenone (compound of the formula (IV)) + Compound of the formula (X) | 10 mg/kg od + 1 mg/kg bid | 15 |

Mortality:

After 40% of the placebo animals had died—the study was generally terminated once 40-50% of the placebo-treated animals had died, which corresponds to a survival rate of 60-50%—the study was terminated and the survival rates of the individual treatment groups were compared to one another. It was found that, in the case of treatment with finerenone (10 mg/kg od) on its own or sGC activator corresponding to the compound of the formula (X) (1 mg/kg bid) on its own, only 20% and 27%, respectively, of the animals died during the study period, which corresponds to survival rates of 80% and 73%, respectively. However, a combination of finerenone (10 mg/kg od)+compound of the formula (X) (1 mg/kg bid) prevented all cases of death throughout the study period and led to significant higher survival with a survival rate of 100% over the study period (Table 2):

TABLE 2

All-cause mortality of L-NAME-treated renin-transgenic rats during the study period.

| Group | Mortality [%] | Significance versus Group A |
|---|---|---|
| Group A | 40 | |
| Group B | 20 | |
| Group C | 27 | |
| Group D | 0 | ** |

In parallel with the complete prevention of cardiovascular and cardiorenal mortality, other parameters of cardiac, cardiovascular and renal function were also improved. These were quantified, for example, by determining protein excretion via the kidney, or by BNP production (BNP=Brain Natriuretic Peptide) in the heart by determination of the BNP plasma concentration.

Proteinuria; Protein/Creatinine Quotient in Urine:

For determining kidney damage in patients, protein excretion in the kidney—which is markedly enhanced in patients—is used. Here, the quotient of protein excreted in the urine and creatinine excreted in the urine, the so-called protein/creatinine quotient, which can be used as a quantitative measure for the kidney damage, is determined. In the animal experiments carried out, too, for example proteinuria, measured as protein/creatinine quotient in urine, has already been lowered significantly on treatment with finerenone (10 mg/kg od) on its own or with the sGC activator corresponding to the compound of the formula (X) (1 mg/kg bid) on its own, by 58% and 8%, respectively. However, here, too, the combination of finerenone (10 mg/kg od)+compound of the formula (X) (1 mg/kg bid) resulted in a markedly more pronounced, highly significant reduction of proteinuria by a total of 85% (Table 3):

TABLE 3 proteinuria (in % reduction from placebo) at the end of the study in L-NAME-treated renin transgenic rats. Data as mean ± SEM; *//*/**** = significant with $p < 0.05/0.01/0.001/0.0001$ (one-way ANOVA + post hoc analysis).

| Group | Protein/creatine quotient- % of group A | Significance versus Group A |
|---|---|---|
| Group A | +/−0 + 15 | |
| Group B | −58 + 16 | * |

TABLE 3-continued proteinuria (in % reduction from placebo) at the end of the study in L-NAME-treated renin transgenic rats. Data as mean ± SEM; *//*/**** = significant with $p < 0.05/0.01/0.001/0.0001$ (one-way ANOVA + post hoc analysis).

| Group | Protein/creatine quotient-% of group A | Significance versus Group A |
|---|---|---|
| Group C | −8 + 20 | |
| Group D | −85 + 2 | *** |

The invention claimed is:

1. A combination comprising (3S)-3-(4-chloro-3-{[(2S,3R)-2-(4-chlorophenyl)-4,4,4-trifluoro-3-methylbutanoyl]amino}phenyl)-3-cyclopropylpropanoic acid of the formula (X)

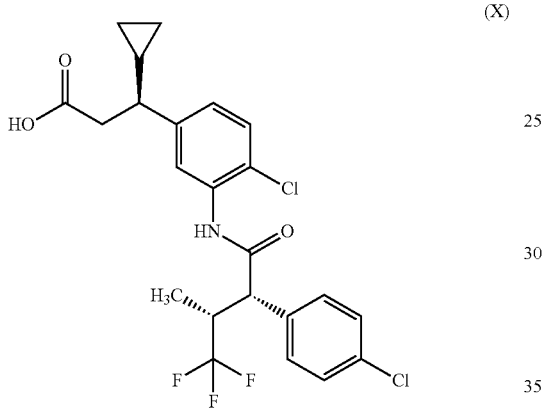

(X)

or a salt, solvate or solvate of a salt thereof and (S)-4-(4-cyano-2-methoxyphenyl)-5-ethoxy-2,8-dimethyl-1,4-dihydro-1,6-naphthyridine-3-carboxamide of the formula (IV)

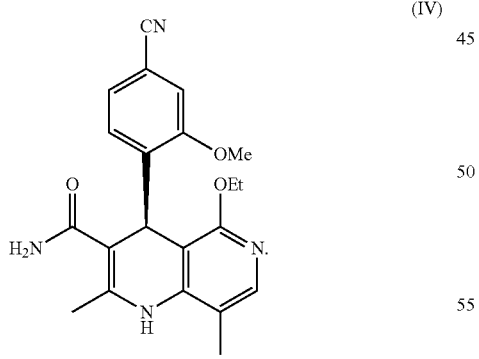

(IV)

2. A pharmaceutical composition comprising the combination of claim 1 combination with an inert, non-toxic, pharmaceutically suitable auxiliary.

3. A pharmaceutical composition comprising the combination of claim 1 in combination with one or more further active compounds selected from the group consisting of ACE inhibitors, angiotensin receptor blockers, combinations of angiotensin receptor blockers and NEP inhibitors (ARNIs), antidiabetics, betablockers, acetylsalicylic acid, diuretics, $I_f$ channel blockers (ivabradin), calcium antagonists, statins, digitalis (digoxin) derivatives, calcium sensitizers, nitrates and antithrombotics.

4. A method for the treatment of a cardiac or cardiovascular disorder that is heart failure with preserved ejection fraction, heart failure with reduced ejection fraction, atrial fibrillation, stroke or atherosclerosis, a renal or cardiorenal disorder that is chronic kidney failure or diabetic nephropathy, or a lung or cardiopulmonary disorder that is pulmonary disease hypertension, in humans and animals, comprising administering a therapeutically effective amount of the pharmaceutical composition according to claim 2 to a human or animal in need thereof.

5. The method of claim 4, wherein 10 to 40 mg of (S)-4-(4-cyano-2-methoxyphenyl)-5-ethoxy-2,8-dimethyl-1,4-dihydro-1,6-naphthyridine-3-carboxamide of the formula (IV) are administered.

6. A kit comprising a pharmaceutical composition comprising (S)-4-(4-cyano-2-methoxyphenyl)-5-ethoxy-2,8-dimethyl-1,4-dihydro-1,6-naphthyridine-3-carboxamide of the formula (IV)

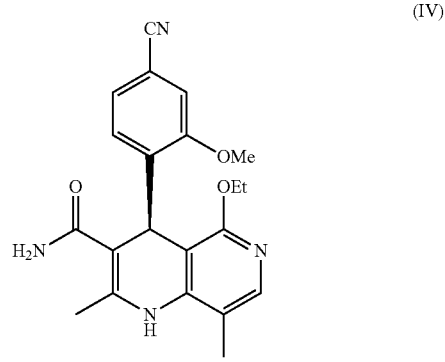 [SMILES: CCOc1ncc(C)c2c1[C@H](c1ccc(C#N)cc1OC)C(C(N)=O)=C(C)N2]

(IV)

and the compound of the formula (X)

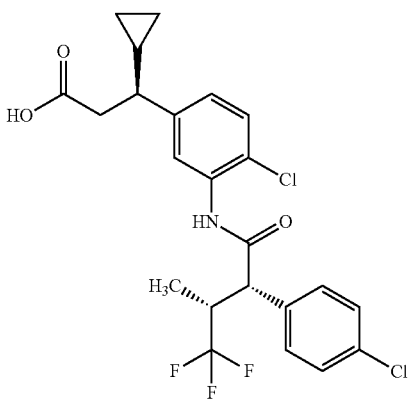

(X)

or a salt, solvate or solvate of a salt thereof.

7. A method for the treatment of a cardiac or cardiovascular disorder that is heart failure with preserved ejection fraction, heart failure with reduced ejection fraction, atrial fibrillation, stroke or atherosclerosis, a renal or cardiorenal disorder that is chronic kidney failure or diabetic nephropathy, or a lung or cardiopulmonary disorder that is pulmonary disease hypertension, comprising administering a therapeutically effective amount of a combination of an sGC activator and a non-steroidal MR antagonist to a human or animal in need thereof, wherein the sGC activator is (3S)-3-(4-chloro-3-{[(2S,3R)-2-(4-chlorophenyl)-4,4,4-trifluoro-3-methylbutanoyl]amino}phenyl)-3-cyclopropylpropanoic acid of the formula (X)

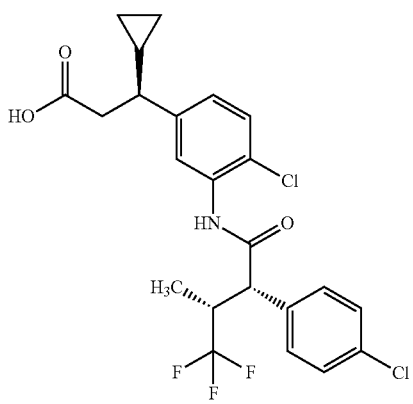

(X)

or a salt, solvate, or solvate of a salt thereof and the non-steroidal MR antagonist is (S)-4-(4-cyano-2-methoxyphenyl)-5-ethoxy-2,8-dimethyl-1,4-dihydro-1,6-naphthyridine-3-carboxamide of the formula (IV)

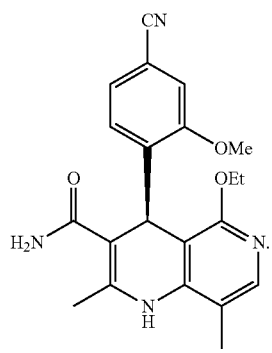

(IV)

8. The method of claim 7, wherein the sGC activator and the non-steroidal MR antagonist are administered simultaneously or sequentially.

9. The method of claim 7, wherein the sGC activator and the non-steroidal MR antagonist are administered in two separate unit dosage forms.

10. The method of claim 7, wherein 10 to 40 mg of (S)-4-(4-cyano-2-methoxyphenyl)-5-ethoxy-2,8-dimethyl-1,4-dihydro-1,6-naphthyridine-3-carboxamide of the formula (IV) is administered.

11. The method of claim 7, wherein the method is for treatment of chronic kidney failure or diabetic nephropathy.

12. The method of claim 7, wherein the method is for treatment of heart failure with preserved ejection fraction, heart failure with reduced ejection fraction, atrial fibrillation, stroke or atherosclerosis.

13. The method of claim 7, wherein the method is for treatment of pulmonary disease hypertension.

* * * * *